United States Patent [19]

Cuadrado et al.

[11] Patent Number: 6,057,450
[45] Date of Patent: May 2, 2000

[54] DERIVATIVES OF PYROGLUTAMINIC ACID PREPARATION PROCESS AND APPLICATIONS

[75] Inventors: Salomon Perez Cuadrado, Madrid; Jesus Hilario Rodriguez Ramos, Getafe, both of Spain

[73] Assignee: Totiam, S.L., Madrid, Spain

[21] Appl. No.: 08/912,731

[22] Filed: Aug. 18, 1997

Related U.S. Application Data

[63] Continuation of application No. 08/696,899, filed as application No. PCT/ES95/00149, Dec. 15, 1995, abandoned.

[30] Foreign Application Priority Data

Dec. 22, 1994 [ES] Spain ...................................... 9402624

[51] Int. Cl.[7] .......................... C07D 401/06; A64K 31/44
[52] U.S. Cl. ........................................ 546/278.4; 514/343
[58] Field of Search .......................... 546/278.4; 514/343

[56] References Cited

PUBLICATIONS

Anderson et al. (1992) J. Immunol. 11:119/.
Bernengo et al. (1984) In: Immunomodulation, Fudenberg et al., rd., Plenum Press, New York, pp.43, 58–65.
Bespalova, G.V. et al. (1981) L.K. Pharm. Chem. J. 15:643–5.
Bespalova, G.V. et l. (1991) Pharm. Chem. J. 25:40–43.
Cohen et al. (1979) JAMA 241:1813–5.
Dillman et al. (1992) J. Immunol. 11:124.
Ganser et al. (1989) Ann. Internal Med. 111:887–92.
Gipponi et al. (1985) Italian J. Surgical Sci. 15:243–8.
Goldstein et al. (1985) 3rd Int. Conf. Immunopharmacol., Florence, 5/6–11, Abst.
Gundermann, K.D. et al. (1964) Chem. Bor. 97:647–52.
Herrmann et al. (1989) J. Clin. Oncol. 7:159–67.
Kalinowski et al. (1988) In: [13]C—NMR—Spektroskopie, John Wiley & Sons, Chichester, New York, pp. 382–3.
Kleinerman et al. (1989) Cancer Res. 49:4665–70.
Komeno et al. (1952) Chem. Abst. 46:Abst.™8118c (J. Pharm. Soc. Japan. 71:646–8).
Mitchell, M.S. (1993) In: Biological Approaches to Cancer Treatment–Biomodulation, Mitchell, M.S. ed., McGraw–Hill, Inc., New York, pp.352, 366, 378,394,398, 476,498,500,514.
Oldman et al. (1983) J. Biol. Response Modif. 2:1–37.
Oettgen et al. (1991) Curr. Opin. Immunol. 3:699–705.
Rahman et al. (1991) J. Immunol. 10:221–5.
Rosenberg, S.A. (1988) In: Important Advances in Oncology, DeVita, Jr. et al. ed., J.B. Lippincott Company, Pennsylvania, pp.217,229,240,252.
Solans et al. (1990) In: Free Papers Printed in Full, U. of Milan, Montorsi et al., ed., Monduzzi Editore S.p.A., Bologna, Italy, pp.I63–67.
Swain, S.L. (1993) J. Immunol. 14:150–4.
Trainin et al. In: Thymic Factor Therapy, Byrom et al. ed., Raven Press, New York, pp.189–97.
Waldman, T.A. (1991) Science 252:1657–62.
Woodruff, M.A. (1980) In: The Interaancer and Host: Its Therapeutic Significance, Grune & Stratton, New York, pp.237–8,249–50,271.
Bespalova, G.V. et al,; Synthesis and Antimic gobial activity of Morphaline derivatives of 2–pyrrolidone and theis Thio Analogs Phasm. Chem. Journal vol. 25, pp. 40–43, 1991.

*Primary Examiner*—Alan L. Rotman
*Assistant Examiner*—Charan Jit S. Aulakh
*Attorney, Agent, or Firm*—Klauber & Jackson

[57] ABSTRACT

The new derivatives of pyroglutaminic acid have the formula (I) wherein $R^1$, $R^2$ and $R^3$ are H or $COR^4$, $R^4$ being lower alkyl or aryl, $A^-$ is $Cl^-$, $CH_3COO^-$ and $OH^-$ and the ondulated line means that the substituent occupies any of the possible spatial positions. The process comprises the reaction of serine with pyridine and acetic anhydrid. These compounds may be applied in immunology as modifiers of the biological immune response, in the "integral" treatment of cancer and prevention or treatment of serious systemic infections in "high risk" patients suffering of chronical diseases and secondary immunodeficiency (cancer, AIDS, Diabetes Mellitus), or primary immunodeficiency (syndromes of DiGeorge, Down).

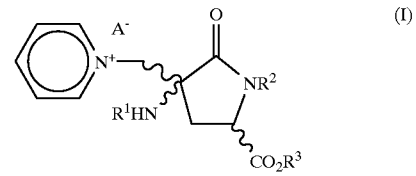

(I)

9 Claims, 19 Drawing Sheets

DERIVATIVES OF PYROGLUTAMINIC ACID PREPARATION PROCESS AND APPLICATIONS

This application is a Continuation of application Ser. No. 08/696,899, filed Aug. 22, 1996 which application is in National Stage of PCT/ES95/00149 which is published as WO96/19473 on Jun. 27, 1996.

TECHNICAL FIELD OF THE INVENTION

The present invention falls within the field of Immunology and, specifically, the modifiers of the biological immune response, "immunomodulators".

Specifically, this invention provides a new generation of biological immune response modifiers very useful in the therapy of chronic diseases, especially cancer and AIDS.

STATE OF THE ARTPRIOR TO THE INVENTION

The natural or acquired resistance of individuals can be seriously affected by multiple intrinisic and extrinsic factors such as genetics, age, general bad nutrition, environment, stress, alcohol, drug addiction, chronic diseases (cancer, diabetes mellitus, sarcoidosis, etc.) chemotherapy agents (cytostatic, antibiotics, etc.) ionizing radiations, severe traumatism and burns, etc. . . .

For many years, many researchers have tried to manipulate the "Immunological Response" (RI) in order to enhance the resistance of patients to pathological processes, the prognosis of which depends to a large extent on the status of their own "Immunological System" (IS). In 1985, J. Héricourt and C. Richet tried to manipulate the RI in patients with melanoma through the heterologous passive Immunotherapy. In 1902 and 1893 to 1929 respectively, E. Von Leyden and F. Blumenthal tested the active Immunotherapy with homologous tumoral cells and W. B. Coley with bacterial toxins, in oncological patients. Afterwards, the administration of serum or blood plasma of donors "immunized" with cancerous cells, "sensitized" autologous or allogeneic lymphocytes, intradermic injection of tumoral cells, etc., in general was very disappointing (M F A Woodruff, 1980). However, the positive results obtained in 24 random studies performed during the 70s (published by W. D. Terry and S. A. Rosenberg 1982) evidence the efficiency of Immunotherapy as a procedure and questions the adequacy of biological crudes and that of the protocols used (R. K. Oldham and R. V. Smalley, 1983).

The recent advances made in Cellular and Molecular Biology, specifically the arrival of monoclonal antibodies (Ac.Mo.) after the hybridomae technology of G. Kölher and C. Milstein in 1975, the individualized clonation and the passage by genetic engineering of eukariotic genes to bacterias, yeasts and even eukariotic cells and the advance with respect to the possibilities offered by new working equipments, either jointly or separately, have made possible the emergence in the market of virtually pure products known as biological response modifiers (BRM), i.e. modifiers of the biological response, currently used mainly in human oncological clinic with different success.

The availability of such products offers new ways to act on the RI and to enhance the resistance of individuals, which is the main objective of the positive Immunomodulation, a term conceptually more precise than that of Biotherapy and broader than that of Immunotherapy itself. The administration of Interferon-alpha (IFN-α) or Interleukin-2 (IL-2) with LAK cells (Lymphokine Activated Killer Cells) as a kind of non-specific Immunomodulation way can cause the regression of tumor metastases (renal carcinoma, no-Hodgkin lymphoma) in patients with favourable prognosis factors (S. A. Rosenberg, 1988).

The adjuvant specific Immunomodulation, either active, passive or adoptive, combined or not with BCG ("Bacillus Calmette-Guérin") and or heterologous monoclonal antibodies (Ac.Mo.) or sensitized lymphocytes can prolong the survival of patients with cancer. However, its use has been seriously limited to a reduced number of institutions and researchers, mainly due to technological difficulties almost impossible to overcome in non-specialized hospitals. The number of cancer patients who benefit from the use of heterologous Ac.Mo. and their conjugated compounds along with toxins ("Immunotoxins") or radionuclides (Radioactive antibodies) is very small yet (F. A. Waldmann, 1991).

The National Biotherapy Study Group of the U.S.A. recommends a selection of patients prior to a continued treatment with IL-2 considering the high toxicity and the low response index observed in 788 patients included between 1985 and 1990 in fifteen clinical trails with high doses of IL-2 associated to LAK cells, TIL (Tumour Infiltrating Lymphocytes) IFNs, TNF (Tumour Necrosis Factor), etc. (R. O. Dillman, 1992). The toxicity seems to be directly proportional to the dose administered. In one series of S. A. Rosenberg 1989, where high doses of IL-2 alone, with LAK cells or TIL were administered to 435 patients with advanced cancer, in 679 occasions there were nine deaths related with the treatment and five patients suffered a myocardial infarction. In 60% of the therapeutical actions hypotension was detected and anemia in 61%, requiring treatment with vasopressors and blood transfusions, respectively. 38% of the patients suffered somnolence, disorientation and coma. Most patients needed symptomatic treatment of fever, emesia, diarrhea, etc. (J. S. Rubin and M. T. Lotze, in Biomodulation, M. S. Mitchell, editor, 1993) and among other rare complications, perforations of colon and of the small intestine were included (D. H. Schwartzentruber et al., 1988 and R. Rahman et al., 1991).

The thymic extracts or factors can restore the RI of patients with primary or secondary immunodeficiencies by promoting cellular differentiation thus expanding the range of T quiescent helper and effector lymphocytes. In "high risk" immunodepressed patients, the THF (Thymus Humoral Factor) and TP-1 (Thymostimulin), respectively, decrease the morbidity and mortality due to severe viral infections (N. Trainin et al., 1984) or post-surgical bacterial sepsis (A. Terrizi et al., 1985; A. Solans et al., 1990, etc). Furthermore, the TFV ("Thymosin Fraction V") combined with Chemotherapy (M. H. Cohen et al., 1979) or Radiotherapy (A. L. Goldstein et al., 1984) in lung cancer, and the TP-1 as adjuvant after surgery in melanoma (M. G. Bernengo et al., 1984) have succeeded to prolong the survival of such patients. TFV obtained from the thymus of calves contains polypeptides with a molecular weight of 1–15 KDa, is practically devoid of toxicity and can cause hyperargic reactions of anaphylactic type (T. Low et al., 1979).

Recently, the agents of several human hematopoietic growth factors have been cloned of which the two most deeply studied have been the rhG-CSF ("recombinant human Granulocyte Colony Stimulating Factor"), and the rhMG-CSF ("recombinant human Macrophage Granulocyte Colony Stimulating Factor") which is currently available for clinical use under three main recombinant forms derived from the "E. coli" (Schering Labs.), yeasts (Immunex Labs.) and "CHO" mammal cells (Sandoz Labs.), respectively (L. M. Souza et al., 1986; J. L. Gabrilove and A. Jakubowski in "Biomodulation" M. S. Mitchell ed., 1993). Their administration to cancer patients in the absence of a myelodepression causes a great increase in the number of circulating (peripheral blood) polymorphonuclear neutrophile (rhG- CSF) or neutrophiles and eosinophile (rhMG-CSF) granulocytes they have managed to decrease the morbidity of the neutorpenia (G. Morstyn et al., 1989; H. F. Oettgen, 1991). Especially, the rhMG-CSF drastically decreases systemic bacterial and viral infections in patients with severe chronic neutropenia (A. Ganser et al., 1989) or after the transplant of bone marrow in patients with malignant lymphoproliferative processes (G Schulz et al., 1991). Its administration prior to chemotherapy notably reduces the duration of the neutropenia. However, 2 out of 14 patients who received rhMG-CSF died from sepsis (K. S. Antheman et al., 1989). The most significant side effects are fever, bone ache, pericarditis, hypotension (G. Morstyn et al., 1989, etc.), nausea and emesis (F. Herrmann et al., 1989, etc.), generalized edema, thrombophlebitis, acute renal failure in one case (K. S. Antman et al., 1989), etc.

The "in vivo" activation of macrophages has not been successful since the life of lymphokines administered intravenously is extremely short (E. S. Kleinerman et al., 1989) while their "in vitro" activation has been successfully achieved through the use of liposomes that contain MDP (Muramil Dipeptide), MTP-PE (analogous lipophilic analogue of MDP), IFNs, etc. Liposomal-MTP-PE (Ciba-Geigy, Ltd., Basel, Switzerland) at the maximum dose of 6 mg/m$^2$ is well tolerated and the main side effects noticed during a phase I trail were chill and fever (80%), fatigue (60%), nausea and emesis (55%), hypo- or hypertension, etc. (J. J. Killion and I. J. Fidler in "Biomodulation", M. S. Mitchell, ed., 1993).

Therefore, the efficacy of experimental immunomodulation has been completely demonstrated. However, the success achieved in oncological clinics, for instance, with the use of the BRM currently available in the market has been, in general, limited to selective populations, sporadic and non-foreseeable, as previously stated.

The manipulation of RI with the exogenous contribution of "cytokines" is not an easy task. In practice, the existing uncertainty regarding the precise regulating role of each cytokine by itself and the (apparent) existence of multiple alternatives pathways for the "in vivo" lymphocyte expansion (M. T. Lotze et al., 1992); the unequivocal cellular and humoral requisites for the effective activation of the primigenial (naive) regulating T lymphocytes (CD 4 cells), which would be the first and unavoidable step to obtain a response, and the factors determining the polarized responses (Th0, Th-1 and Th-2 patterns) of the CD4 T cells (S. L. Swain, 1993), etc. . . . would together make it difficult to select a strategy up to the point that the pretention to guess the adequate BRM, dose and time in each case as well as to predict the results is just an utopia. The toxicity of some BRM, similar to that of the cytotoxic agents common in antineoplastic chemotherapy; the frequent production of anti-IFNα, anti-Ac.Mo., anti-TFV, anti-TP-1, etc. specific antibodies that apart from interfering with their bioavailability and efficacy provoke hyperergic type reactions; the technological difficulties and the financial cost—sometimes unsurmountable—of certain protocols etc., make it necessary to develop and incorporate more effaceous and safer new immunomodulators.

The present invention overcomes the different therapeutical limitations that the above-mentioned BRM currently have. Some of them are due to the biological activity, the bioavailability and their indications; others to the systemic toxicity (in some cases similar to that of cytotoxic pharmaceutical products) and the production of specific antibodies such as anti-IFNα, anti-Ac.Mo., anti-TFV, etc. that can provoke severe anaphylactic type hyperergic reactions, etc.

The BRM-BLAS products afforded by the present invention represent a peerless new generation of BRM-synthetic agents. Such compounds overcome the natural limitations of thymic extracts and factors, i.e. "immunorestorers", by potentiating the RLP-I (Non-specific Lymphoproliferative Response) and by increasing the number of circulating (peripheral) blood lymphocytes in normal individuals so that they exceed the physiological basal values and are perfectly tolerated. As it will be seen below, these products have been repeatedly used during the last two years in the same animals without impairing their normal activity and with a complete absence of undesired side effects. Furthermore, the administration of Swiss mice of a dose thousand of times higher than the therapeutical or biological effective doses in the case of rabbits—without any noteworthy evidence of pathological signs—also guarantee their satisfactory tolerance.

Finally, with respect to the "CSFs", the complementary, non-competitive or substitute use of them should logically be considered. Each has its precise indications in different clinic situations.

DETAILED DESCRIPTION OF THE INVENTION

Figure 1:
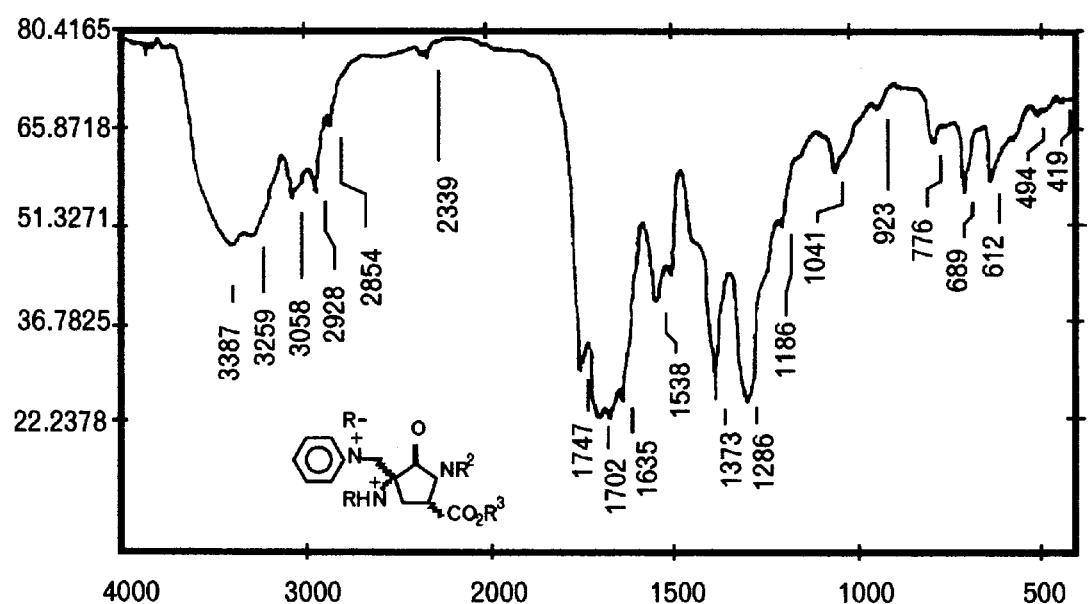
FIG. 1.—It shows the IR spectrum of the basic crude product.

This invention affords a new generation of BRM agents, biological response modifiers with a marked positive immunomodulator activity, more efficaceous and safer that those currently available in the market. They are new original derivatives of the pyroglutamic acid, obtained from chemical synthesis either with chloride (CL—) or acetate ($CH_3COO$—) anions, as pyridine salts.

The basic molecular structure, the cation, is formed of a pyridine ring (N-methylpyridine) and another dissubstituted lactamic ring (pyroglutamic acid) with two stereogenous centres and three potentially acetylable groups, two of them nitrogenous, that give rise to different stereoisomeric compounds and their acetylatable derivatives, all of which are included within the scope of the present invention. The exact molecular mass corresponding to the main stable compounds, excluding the anion, is 236.10385 (average of nine measures), 278.11387 (average of eleven measures) and 320.12480 (average of eight measures). The respective molecular formulae are: $C_{11}H_{14}N_3O_3$ (theoretical exact mass: 236.10357; δ−1.4 ppm), $C_{13}H_{16}N_3O_4$ (theoretical exact mass: 278.11408; δ 0.8 ppm) and $C_{15}H_{18}N_3O_5$ (theoretical exact mass: 320.12465; δ−0.5 ppm).

Purified dry products are crystalline, white, very hygroscopic, deliquescent and when heated they become caramel-like and are decomposed without melting above 180° C. They are water and alcohol soluble and practically insoluble in acetone and ether among other organic solvents. In an aqueous solution their maximum UV absorption peak between 259–260 nm.

The most peculiar and outstanding biological characteristics of such BRM agents are their marked "in vivo" and "in vitro" immunomodulating activity along with their perfect tolerance. All of them increase the non-specific lymphoproliferative response (RLP-I) to the phytohemagglutinin (PHA) in "in vitro" cultures of human lymphocytes (healthy persons—blood donors) and the absolute values of the circulating peripheral blood leukocytes, especially of lymphocytes, in experimental animals (New Zealand's albino and giant rabbits), asymptomatic, which effect is biologically and statistically significant.

In summary, this invention covers different original BRM compounds, indistinctly described as salts of 1-(1-amino-3-aza-4-carboxyl-2-oxycyclopentyl) methylpyridinium or derivatives of 4-amino-4-(pyridiniomethyl) pyroglutamic acid with the following general formula (I):

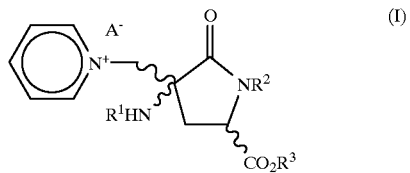

wherein $R^1$, $R^2$ and $R^3$ are independently selected between H and $COR^4$, where $R^4$ is a lower alkyl or aryl and A— is an anion selected between Cl—, $CH_3COO$—, OH—; and the undulated line means that the relevant substituent may occupy any of the possible spatial positions, without excluding oligomeric products of the basic structure. Their more outstanding common denominator or biological activity is a significant enhancement of the "in vitro" RLP-I induced by the PHA and of the absolute number of circulating peripheral blood lymphocytes in healthy individuals, exceeding the physiological baseline values.

Therefore, they have been jointly designated by the generic name of "BLAS" (Blood Lymphocyte Augmenting Substances) followed, in each case, for their specific identification by the number of the nominal value of the molecular mass of the cation and, in brackets, the signs (Cl) and (Ac) of their respective chloride and acetate anions.

The procedure of this invention to obtain the said products incorporates an original method for the initial chemical synthesis of the basic crude and the concatenated preparation from it of the new BRM-BLAS compounds.

The experimental conditions for the synthesis of the crude product are broad with regard to the quantities and proportions of the reagents used, reaction time, temperature, etc. Briefly, the selected quantity of L-serine is mixed with a molar excess of acetic anhydride (5.6–4.4 moles/mol) and pyridine (1.6–1.9 moles/mol). The reaction can be performed between time and temperature intervals that respectively vary from 15 minutes to 18 hours and from 35° C. to the reflux temperature of the mixture, although it is preferable to heat it during 20–30 minutes at 80°–90° C. with a continuous agitation. Once the mixture of the reaction is cool, the crude product is precipitated with ethylic ether, washed with it or with a mixture of ether-acetone, dried and it can be stored at room temperature during several years without noticeable alterations or damages. Even though the experimental conditions are essentially the same than those of the Dankin-West reaction ("alpha-aminoacids with acetic anhydride with the presence of a base"; H. D. Dankin and R. West, 1928), the presence of a methyl ketone is not detected in the product. Instead, a mixture of the compounds that constitute the principal crude product of this invention appears. The crude product dry powder is of a creme-beige colour, soluble in water and alcohol and from such solutions it can be obtained in a crystallized form. The UV spectrum has no defined peak and shows a plateau between 256–259 nm. However, the IR (KBr) spectrum shows many characteristics and intense bands at 1286, 1373, 1538, 1635, 1665, 1702 and 1747–1756 $cm^{-1}$ (Table I and FIG. 1), fully coincident with the general formula (I) given for the BRM-BLAS compounds.

The purification of the crude product can be performed by the usual adsorption chromatography techniques with activated carbon in a matrix either of cellulose, silica gel, pevikone, etc. or a combination of all. The molecular structure of such compounds has been elucidated by Nuclear Magnetic Resonance ($^1H$ and $^{13}C$-NMR) on $D_2O$ solutions in BRUKER AC-200 and AMX-300 spectrometers; Mass spectrometry (EM and EMAR) with Cs ions on a matrix of m-nitrobenzylic alcohol, "LSIMS" ("Liquid Secondary Ion Mass Spectrometry") method, in an VG-AutoSpec spectrometer; Infra-red (IR) spectroscopy in a solid medium (KBr) tablet with the FTIR spectrophotometer, BRUKER brand, IFS 85 model and Elemental Analysis with a PERKIN ELMER 2400 CHN elemental analyzer.

TABLE 1

| INFRA-RED SPECTROSCOPY (II) | | | | | | |
|---|---|---|---|---|---|---|
| | | BIOLOGICAL RESPONSE MODIFIERS | | | | |
| PRINCIPAL B | CRUDE | BLAS - 236 | | BLAS - 278 | | BLAS - 320 |
| $\infty-1$ | PRODUCT | (Cl) | (Ac) | (Cl) | (Ac) | (Cl) (Ac) |
| 1182–1195 | d | d | d | d | d | d d |
| 1290–1304 | FF | d | d/m | d/m | m/f | f F |
| 1373–1390 | FF | === | F | === | f/F | F F |
| 1391–1399 | === | m | === | m/f | === | === === |

TABLE 1-continued

INFRA-RED SPECTROSCOPY (II)

| PRINCIPAL B | CRUDE PRODUCT | BIOLOGICAL RESPONSE MODIFIERS | | | | | |
|---|---|---|---|---|---|---|---|
| | | BLAS - 236 | | BLAS - 278 | | BLAS - 320 | |
| ∞−1 | | (Cl) | (Ac) | (Cl) | (Ac) | (Cl) | (Ac) |
| 1490–1491 | f | f/F | f/F | f/F | f/F | f/F | F |
| 1538–1550 | F | === | === | === | === | F | F |
| 1601–1611 | F | === | FF | FF | FF | === | FF |
| 1631–1636 | FF | F | FF | FF | FF | FF | FF |
| 1660–1665 | FF | === | === | FF | FF | FF | FF |
| 1698–1709 | FF | === | FF | FF | FF | FF | FF |
| 1727 | === | FF | === | === | === | === | === |
| 1745–1765 | F | === | === | === | === | F | F |
| 2955–3050 | d | m/f | === | m/f | === | === | d |
| 3200–3500 | d | m/f | m/f | m/f | m/f | m/f | m/f |

FF: very strong; F: strong; f: moderately strong; m: moderate; d: weak

PREFERRED EXECUTION MODES OF THIS INVENTION

In the following examples the present invention is illustrated with more detail, making reference to the specific compounds covered by it and to one specific case of the preparation procedure.

EXAMPLE NO. 1

BRM-BLAS 236 (Cl)

This name covers the A and B isomer compounds called (IUPAC-386.3) "1-(1-ammonium-3-aza-4-carboxyl-2-oxycyclopentyl) methylpyridinium" dichloride or "4-ammonium-4-(1-pyridiniomethyl) pyroglutamic acid dichloride" with the molecular formula $C_{11}H_{15}Cl_2N_3O_3.H_2O$, their elemental analysis of which, theoretical versus found, (in brackets) is C 40.51% (40.94%), H 5.25% (5.57%), N 12.88% (12.93%), Cl 21.74% and O 19.62%. In aqueous solution they have a maximum UV absorption peak at 259.5 nm and follow the Lambert-Beer Law for concentrations ranging between 10–100 micrograms/ml.

Figure 2:
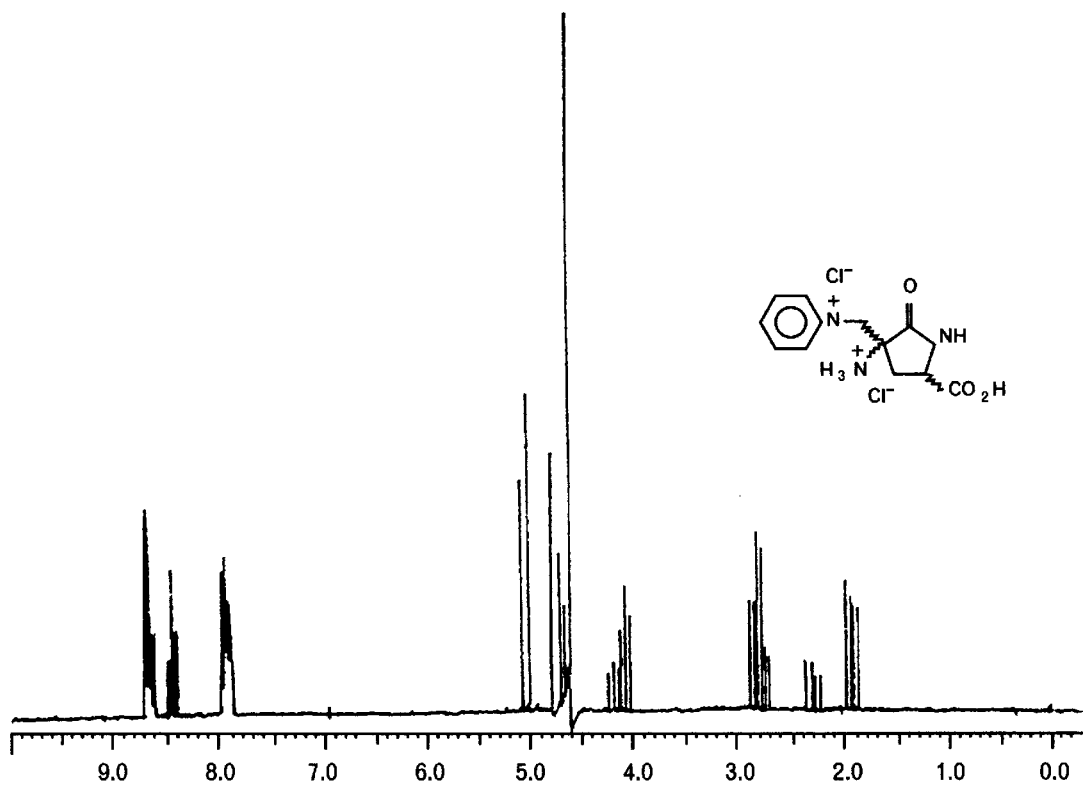
FIG. 2.—It shows the $^1$H-NMR spectrum of the BRM-BLAS 236 (Cl) compounds.
Figure 3:
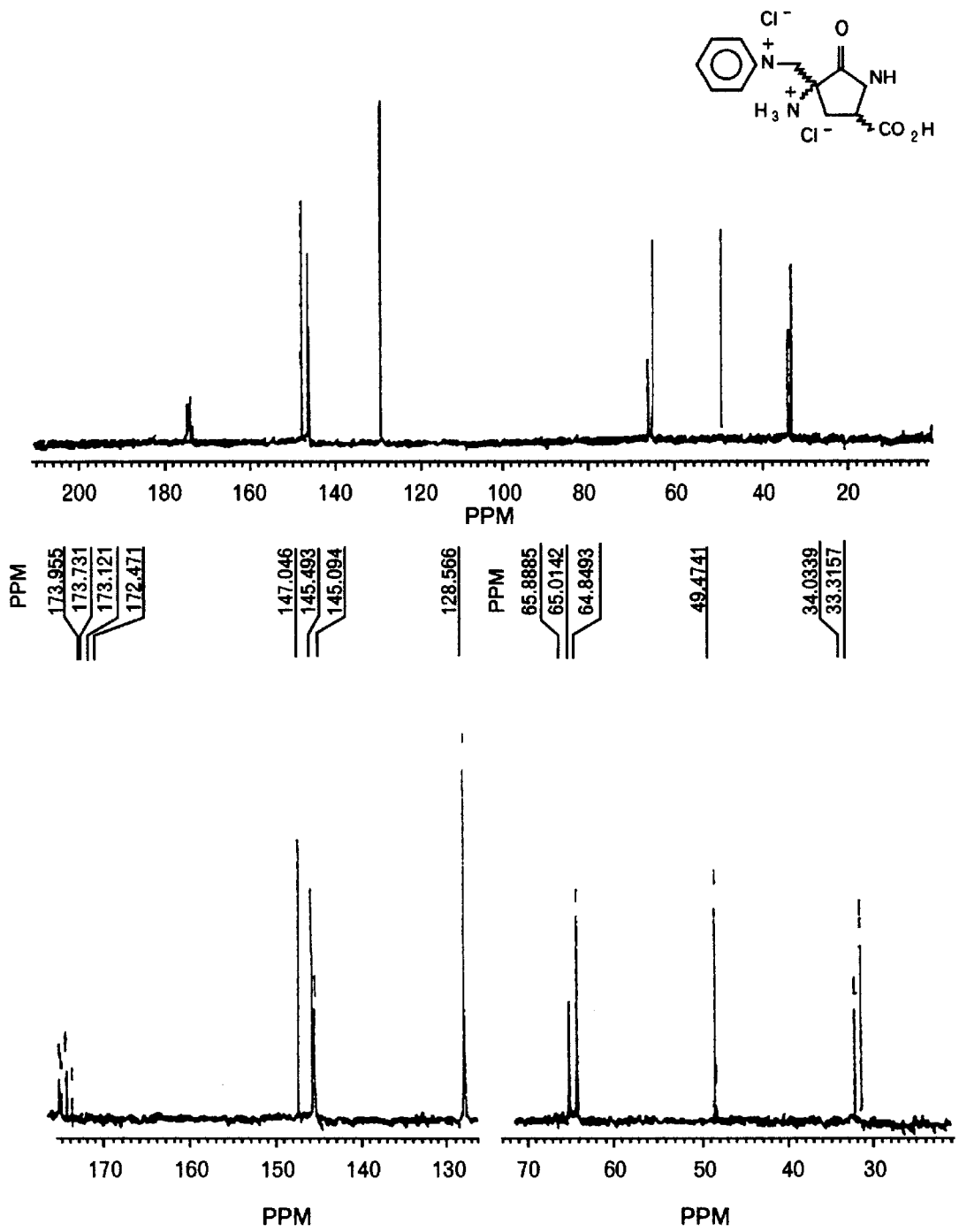
FIG. 3.—It shows the $^{13}$C-NMR spectrum of the BRM-BLAS 236 (Cl) compounds.

They can be obtained as a hydrochloride, monohydrated, by acid hydrolysis of the purified acetylated derivatives or directly from the crude product. The experimental conditions of hydrolysis are very broad. It can be performed with hydrochloric acid from 0.6N to 3.0N at 100°–115° C. during 2 to 16 hours, or at lower temperatures during longer reaction times. From a sample with 1.0 g of the semipurified acetylated derivatives dissolved in 40 ml of a 0.9N solution of hydrochloric acid and heated at 105° C. during 165 minutes, 250 mg of a mixture of A (40%) and B (60%) pure compounds can be obtained without any other sign in the $^1$H-NMR and $^{13}$C-NMR spectra that could correspond to impurities of another organic compound (FIGS. 2 and 3). They are mainly recovered from the chromatographic column hydrophilic phase eluate.

The spectroscopic data and the elemental analysis of the A and B diastereoisomer compounds fully confirm their molecular structure represented in the formula (II).

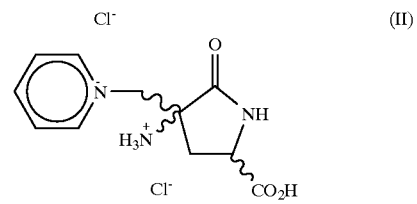

(II)

The tabulated data of the $^1$H-NMR and $^{13}$C-NMR of Table II are self-explaining.

TABLE II

BRM - BLAS 236 (Cl) - A, B DIASTEREOISOMERS

| $^1$H—RMN | | | $^{13}$C—RMN | |
|---|---|---|---|---|
| δ (ppm) | Multiplicity$_{(W,H_2)}$ | Integral | δ (ppm) | Assignment (Dept) |
| 8.66 A | m$^a$ | 2H | 174.0 | C |
| 8.63 B | m$^b$ | 2H | 173.7 | C |
| 8.44 A,B | m$^a$ | 1H + 1H | 173.1 | C |
| 7.96–7.87 A,B | m | 2H + 2H | 172.5 | C |
| 5.03 A,B | d(14.0) | 1H + 1H | 147.0 | CH |
| 4.73 A | d(14.0) | 1H | 145.5 | CH |
| 4.62 B | d(14.0) | 1H | 145.1 | CH |
| 4.18 B | dd(10.3; 8.8) | 1H | 123.6 | CH |
| 4.06 A | dd(10.4; 9.0) | 1H | 65.9 | CH2 |
| 2.82 A | dd(15.5; 9.0) | 1H | 65.0 | CH2 |
| 2.75 B | dd(14.0; 8.8) | 1H | 64.8 | C |
| 2.28 B | dd(14.0; 10.3) | 1H | 49.5 | CH2 |
| 1.92 A | dd(13.5; 14.4) | 1M | 34.0 | CH2 |
| | | | 33.3 | CH2 |

$^a$pseudodoublet; $^b$pseudotriplet

In synthesis, the protonic spectrum clearly evidences a CH—CH$_2$ aliphatic fragment linked by the first carbon to a heteroatom. The isolated AB system, strongly dis-screened and with a high coupling constant corresponds to a methylene group, having discarded a double CH=CH link through the experiment of correlation $^1$H/$^{13}$C to a link. The $^{13}$C-NMR spectrum corroborates such groupings and the CH signs respectively assigned to the aromatic carbons are in line with the values tabulated for the N-methylpyridine cation by Hans-Oto Kalinowski et al. (1988) (Refer to Table II). The EM mass spectrum confirms the presence of the pyridinium ring in the molecular structure of such compounds and their nominal mass, fragments at m/z 80 (protonated adduct of the pyridine) and at m/z 236, respectively, as shown in Table III.

TABLE III

MASS SPECTROSCOPY (EM)

| | BIOLOGICAL RESPONSE MODIFIERS | | | | | |
|---|---|---|---|---|---|---|
| RELEVANT PEAKS | BLAS - 236 | | BLAS - 278 | | BLAS - 320 | |
| (m/z) | (Cl) | (Ac) | (Cl) | (Ac) | (Cl) | (Ac) |
| 80 | 9% | 40% | 25% | 37% | 39% | 96% |
| 199 | === | === | 7% | 28% | 15% | 50% |
| 236 | 33% | 100% | 36% | === | === | === |
| 241 | === | === | === | === | 6% | 12% |
| 278 | === | === | 53% | 100% | 58% | 24% |
| 320 | === | === | === | === | 100% | 100% |
| 513 | === | === | 3% | === | === | === |
| 553 | === | === | 3% | 7% | === | === |

TABLE III-continued

MASS SPECTROSCOPY (EM)

BIOLOGICAL RESPONSE MODIFIERS

| RELEVANT PEAKS | BLAS - 236 | | BLAS - 278 | | BLAS - 320 | |
|---|---|---|---|---|---|---|
| (m/z) | (Cl) | (Ac) | (Cl) | (Ac) | (Cl) | (Ac) |
| 597 | === | === | === | === | 5% | === |
| 639 | === | === | === | === | 5% | === |

(%): Relative intensities of signals/The BRM-BLAS 320 (Ac) spectrum includes only up to m/z 500

Likewise, the exact mass of the cation obtained in the high resolution EMAR spectrum fully coincides with the theoretical of the molecular formula inferred from the exact mass (δ–1.4 ppm), excluding the anion.

The data of the IR spectrum are also concordant. The wide and structured band between 2,200 and 3,500 cm$^{-1}$ is characteristic of the aminoacid hydrochlorides and the single non-resolved band at 1,727 cm$^{-1}$ of the carbonyl, lactamic and carboxylic groups (Table I). The different stereochemistry around one or both chiral centres would be the main reason for the existence of the A and B isomeric compounds, diastereoisomers.

EXAMPLE NO. 2

BRM-BLAS 236 (Ac)

These compounds come from the BRM-BLAS 236 (Cl) described above where the chloride molecular anion (Cl—) has been replaced by the acetate (CHCOO—). They are called "1-(1-amino-3-aza-4-carboxyl-2-oxycyclopentyl) methyl]pyridinium acetate" or "4-amino-4-(1-pyridiniomethyl) pyroglutamic acid acetate". The molecular formula is $C_{13}H_{17}N_3O_5$.

The exchange of the molecular anion can be made at room temperature from a 2% aqueous solution of the BRM-BLAS 236 (Cl) compounds to which first NaOH ($^1$N) is added in an amount enough to obtain a pH>9 and then acetic acid until returning the solution to a pH<4. The BRM-BLAS 236 (Ac) compounds purified by chromatography can be obtained free from other salts with an approximate yield of 80% of the sample.

In aqueous solution, their maximum UV absorption peak is at 259.5 nm and they follow the Lambert-Beer law for concentrations between 10–100 micrograms/ml.

Their molecular structure or linkage formula is represented in the formula (III)

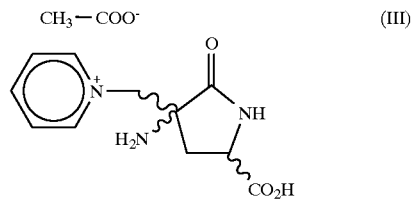

Without it being possible to discard their corresponding ammoniacal salt.

The spectroscopic data of $^1$H-NMR and $^{13}$C-NMR are fully concordant or can be referred to those of the previously described BRM-BLAS 236 (Cl) compounds from which they derive (Table II; FIGS. 2 and 3).

Figure 4:
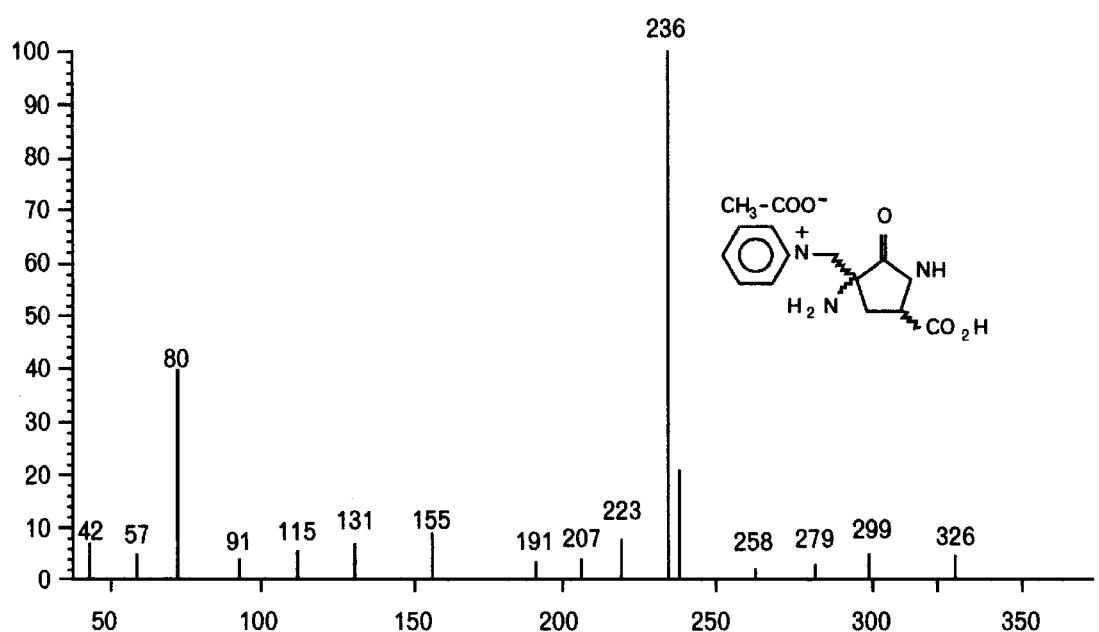
FIG. 4.—It shows the EM spectrum of the BRM-BLAS 236 (Ac) compounds.

Obviously, the EM spectra—since they have all the same molecular cation—are exactly the same (Table III; FIG. 4).

Figure 5:
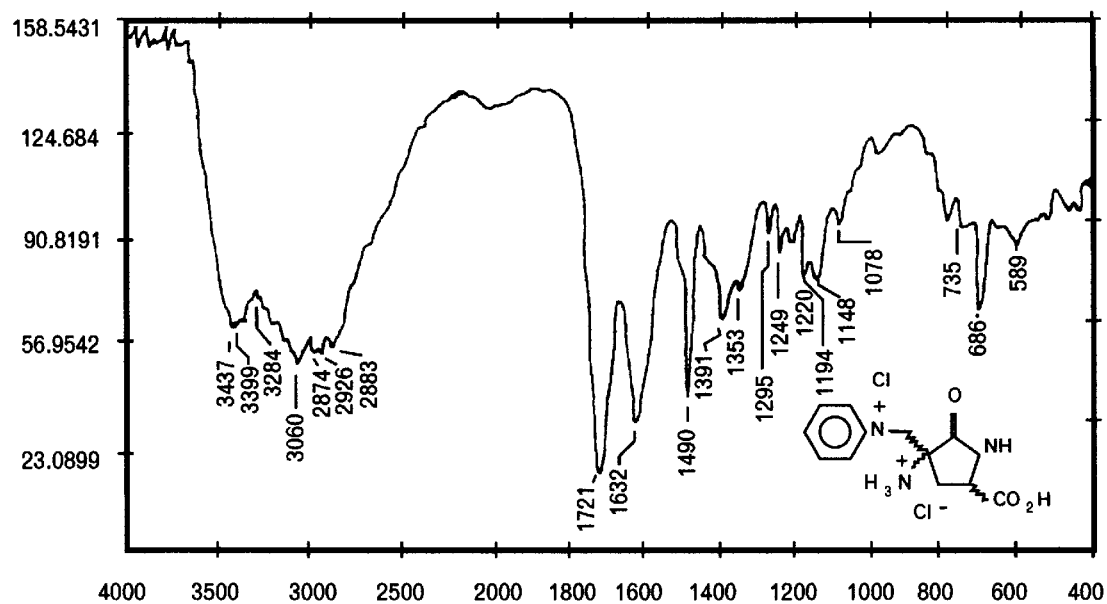
FIG. 5.—It shows the IR spectrum of the BRM-BLAS 236 (Cl) and BRM-BLAS 236 (Ac) compounds for comparison purposes.
Figure 5:
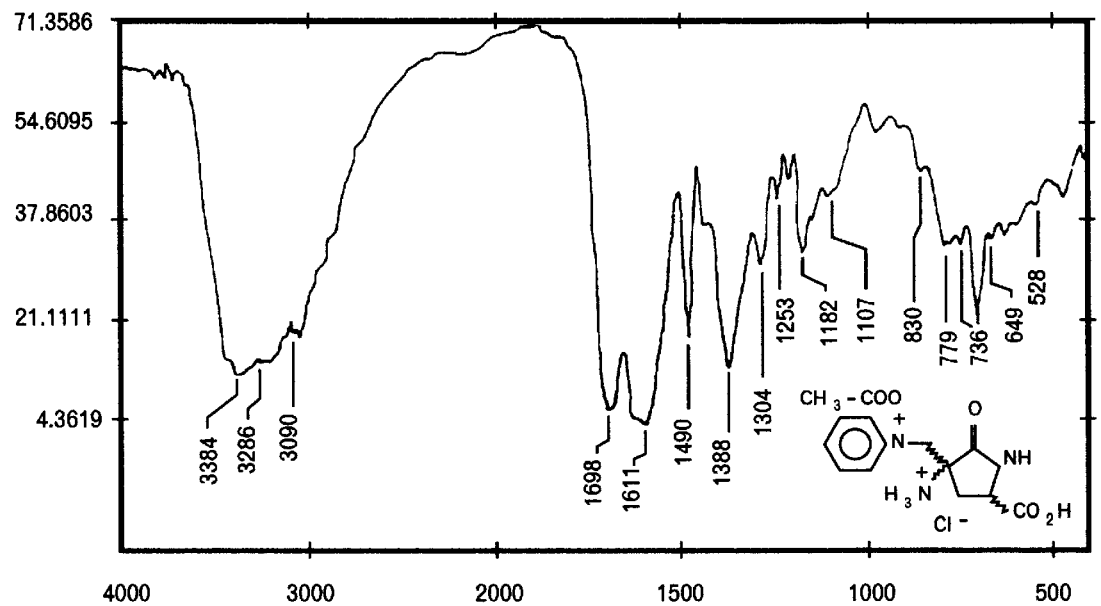

However, the IR spectrum of the BRM-BLAS 236 (Ac) compounds shows strong and very strong bands at 1388 cm$^{-1}$ and between 1500–1700 cm$^{-1}$, which are the characteristics of the methyl and carbonyl groups of their own molecular anion, which obviously are absent in the original compounds from which they derive (Table I; FIG. 5).

EXAMPLE NO. 3

BRM-BLAS 278 (Cl)

This name includes the monoacetylated derivatives of the BRM-BLAS 236 (Cl) compounds described above. They are called "1-(3-acetyl-1-ammonium-3-aza-4-carboxy-2-oxycyclopentyl) methyl]pyridinium dichloride" or "1-acetyl-4-ammonium-4-(1-pyridiniomethyl) pyroglutamic acid dichloride", of the molecular formula $C_{13}H_{17}Cl_2N_3O_4$.

They can be directly obtained as main product in the form of hydrochlorides by partial acid hydrolysis of the diacetylated compounds or of the crude product and indirectly as a subproduct in the preparation of the BRM-BLAS 236 (Cl) compounds. They are mainly recovered from the chromatographic column mainly in the lipophilic phase eluate. The experimental conditions of the partial hydrolysis are somewhat narrow. It can be made with hydrochloric acid from 0.03 N to 0.07 N at 100–115° C. during 16 to 24 hours. From a sample of 2 g of the crude product dissolved in 100 ml of a 0.05 N solution of hydrochloric acid, heated at 105° C. during 18 hours, approximately 600 mg of the purified product (30%) can be obtained.

In aqueous solution, their maximum UV absorption peak is at 259.5–260 nm and they follow the Lambert-Beer law for concentrations between 10–100 micrograms/ml.

In general, the $^1$H-NMR and $^{13}$C-NMR spectra are referrable to those of the BRM-BLAS 236 (Cl) already described with the exception of the presence of four isomeric compounds with an additional methyl group for each of them, and the molecular structure of which corresponds to the structural formula (IV)

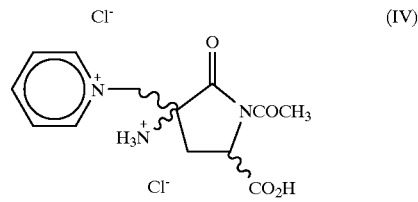

The identification of up to six isomers in some sample could be due to the presence of acyclic or dimeric nature compounds derived from the opening of the lactamic ring.

The exact cation mass obtained in the high resolution spectrum EMAR of the isomeric mixture, practically coincides with the theoretical calculated from the molecular formula obtained for the exact mass (δ 0.8 ppm), excluding the anion.

The comparative study of the respective EM spectra of the BRM-BLAS 278 (Cl) and BRM-BLAS 236 (Cl) compounds evidences their the inter-relationship. The highest intensity peak at m/z 278 corresponding to the mass of the molecular cation of the BRM-BLAS 278 (Cl) compounds takes place after losing 42 uam at m/z 236, precisely the nominal mass of the molecular cation of the BRM-BLAS 236 (Cl) compounds. Therefore, the former are undoubtedly monoacetylated derivatives of these compounds.

On the other hand, the loss of 79 uam from the m/z 278 main peak giving rise to the m/z 199 along with the signal at m/z 80 (protonated pyridine adduct) clearly reveals the presence of the pyridinium ring in their molecular structures (Table III).

Figure 6:
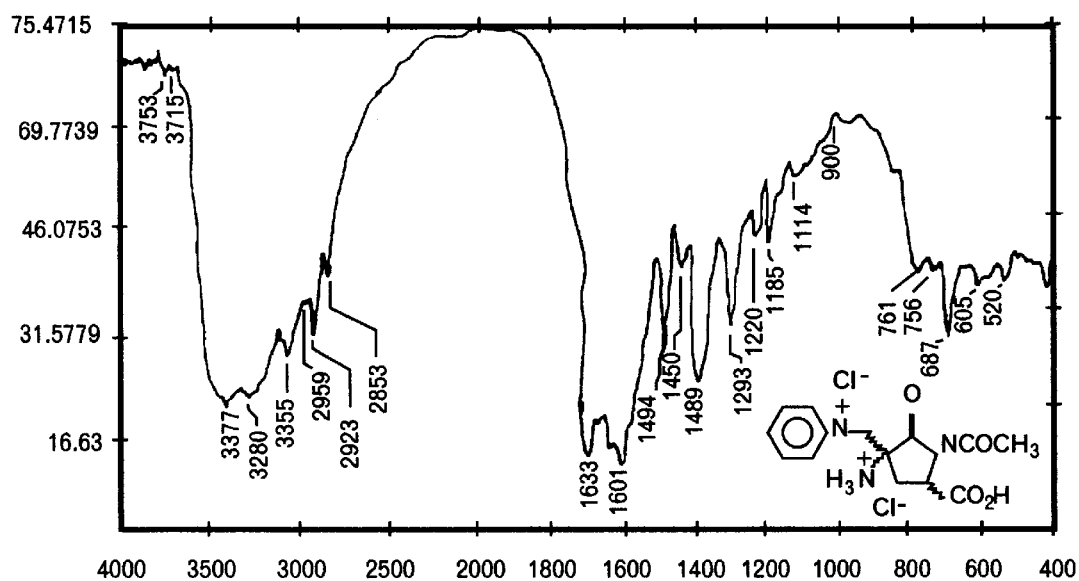
FIG. 6.—It shows the IR spectra of the BRM-BLAS 278 (Cl) and BRM-BLAS 278 (Ac) compounds for comparison purposes.
Figure 6:
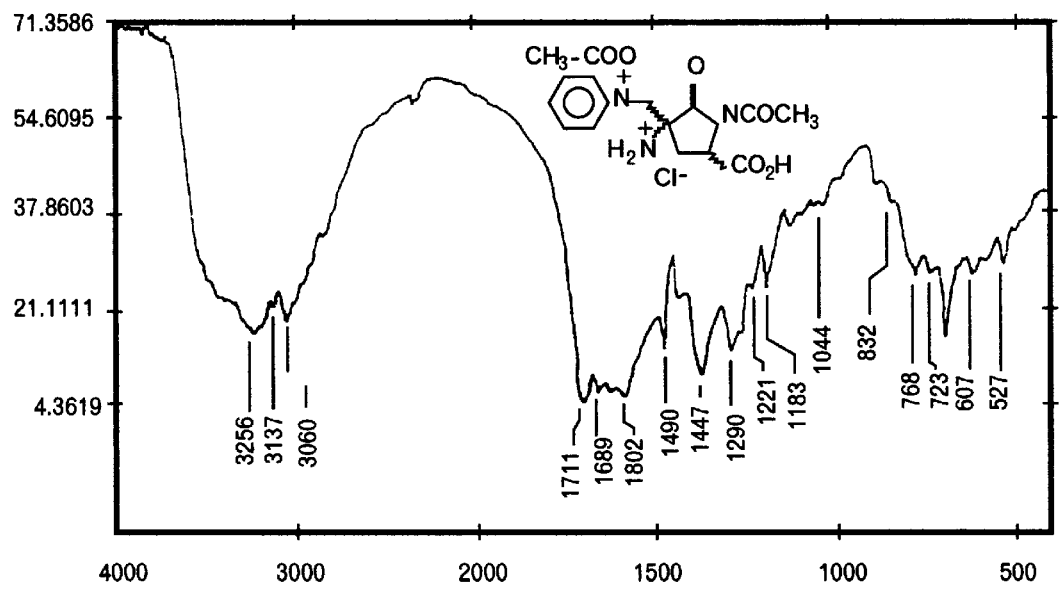

The IR spectrometry is concordant with the position assigned to the acetyl group of the BRM-BLAS 278 (Cl) compounds, since such compounds lack the strong band at 1540 cm$^{-1}$ (band II, in solid phase) characteristic of the N—H band combination and M—C tension in the amides and "$R_1$—CO—NH—$R_2$" related compounds and which, on the other hand, is evident in the diacetylated compounds from which they derive by partial acid hydrolysis (Table I; FIG. 6).

EXAMPLE NO. 4

BRM-BLAS 278 (Ac)

Under this name the monoacetylated derivatives of the BRM-BLAS 236 (Ac), described above, are included. They are called "1-(3-acetyl-1-amino-3-aza-4-carboxyl-2-oxycyclopentyl) methyl]pyridinium acetate" or "1-acetyl-4-amino-4-(1-pyridiniomethyl) pyroglutamic acid acetate", of the molecular formula $C_{15}H_{19}N_3O_6$. In an aqueous solution, their maximum UV absorption peak is at 259.5–260 nm and they follow the Lambert-Beer law for concentrations between 10–100 micrograms/ml.

They can be indistinctly obtained through heating the crude product during a long period of time in an aqueous solution (pH 4) or by replacement of the molecular anion of the BRM-BLAS 278 (Cl) compounds described above, by the acetate ion.

From a sample of 2 g of the crude product dissolved powder in 100 ml of water, after 18 hours at 110° C., approximately 500–600 mg (25–30%) of purified product can be obtained from the chromatographic column mainly in the lipophilic phase eluate, immediately after the hydrophilic phase.

The molecular structure or the structural formula of these compounds is represented in the formula (V).

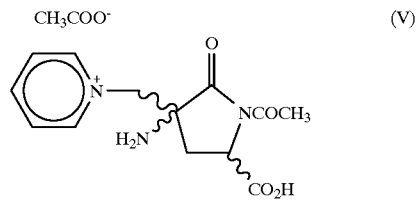

(V)

Without it being possible to discard their corresponding ammoniacal salt.

The spectroscopic data of these compounds are also concordant with the molecular structure shown. In general, they show the same type of compounds than the BRM-BLAS 278 (Cl) with the exception of a greater number of signals corresponding to the acetate molecular anion. The pattern of the IR spectrum is practically identical to that of such compounds (FIG. 6), both having the same number of bands (Table I).

Figure 7:
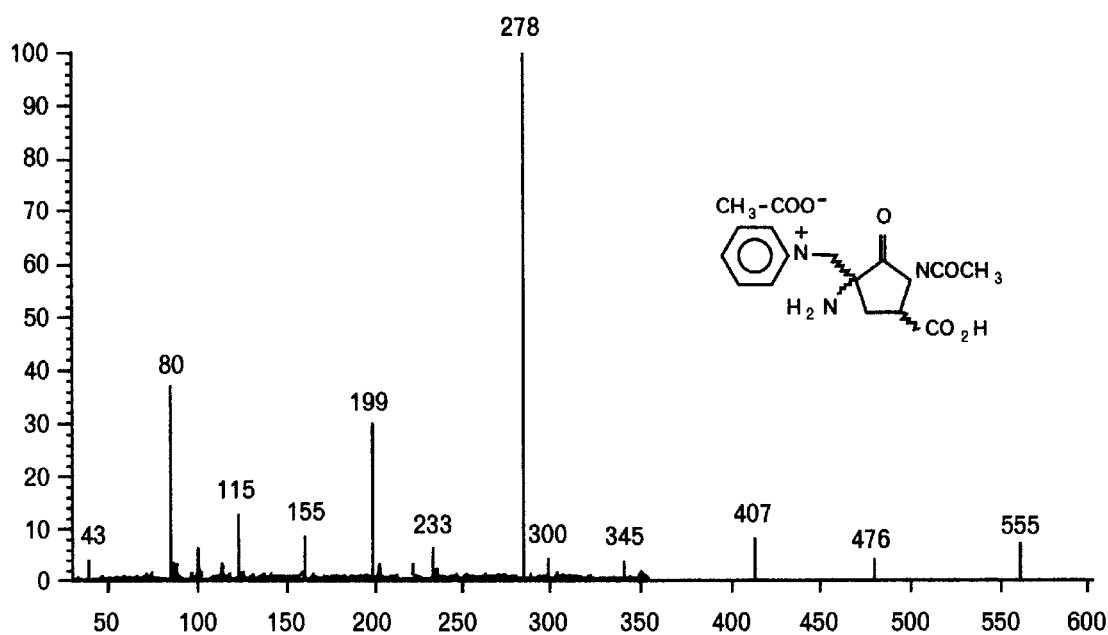
FIG. 7.—It shows the EM spectrum of the BRM-BLAS 278 (Ac) compounds.

The EM spectrum shows a main peak at m/z 278 which represents the nominal mass of the molecular cation and another two at m/z 199 and m/z 80 resulting from the fragmentation of the main one in two (FIG. 7). However, there is no trace of the peak at m/z 236, a contaminant that can appear with the BRM-BLAS 278 (Cl) compounds when they are obtained as a byproduct from the preparation of the BRM-BLAS 236 (Cl) compounds (Table III).

EXAMPLE NO. 5

BRM-BLAS 320 (Ac)

Under this name the diacetylated derivatives of the BRM-BLAS 236 (Ac) are included. The are called "1-(3-acetyl-1-acetylamino-3-aza-4-carboxy-2-oxycyclopentyl) methyl] pyridinium acetate" or "1-acetyl-4-acetylamino-4-(1-pyridiniomethyl) pyroglutamic acid acetate", of the molecular formula $C_{17}H_{21}N_3O_7$. In aqueous solution, their maximum UV absorption peak is at 260 nm and they follow the Lambert-Beer law for concentrations between 10–100 micrograms/ml.

They can be directly obtained from the crude product and if wanter from the BRM-BLAS 320 (Cl) purified compounds by replacing the molecular anion by the acetate ion. From a sample of 2 g of the crude product dry powder in a 2% aqueous solution, approximately 500–600 mg (25–30%) of purified product can be obtained from the chromatographic column mainly in the lipophilic phase eluate.

The molecular structure or the structural formula of these compounds is represented in the formula (VI).

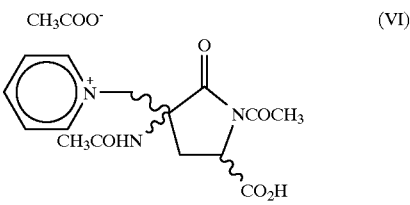

(VI)

Figure 8:
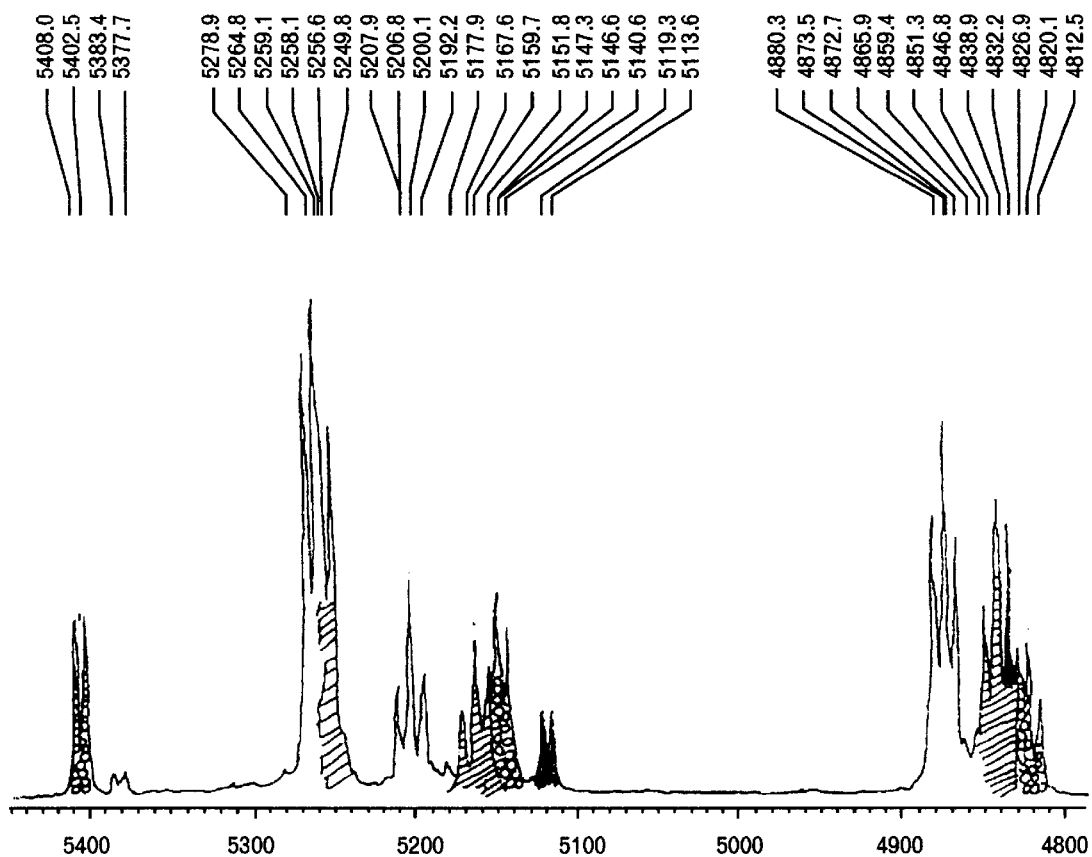
FIG. 8.—It shows the $^1$H-NMR spectrum of the isomeric BRM-BLAS 320 (Ac) compounds.

The pattern of the $^1$H-NMR spectra of the BRM-BLAS 320 (Ac) compounds, with regard to the multiplicities of signals and chemical shifts at which they appear, is totally referrable to that of the BRM-BLAS 236 (Cl) and BRM-BLAS 278 (Cl) compounds described above, except that it presents a greater number of signals corresponding to the methyl and carboxyl groups of the molecular anion and to the acetyl residues. Their analysis by $^{13}$C-NMR, including DEPT, also supports the presence of the fragments observed in the most simple monoacetylated and disacetylated compounds. Structurally, they are in fact the same kind of compounds, four isomers being observed (FIG. 8), with the presence therein of two groups of acetyl signals.

Figure 9:
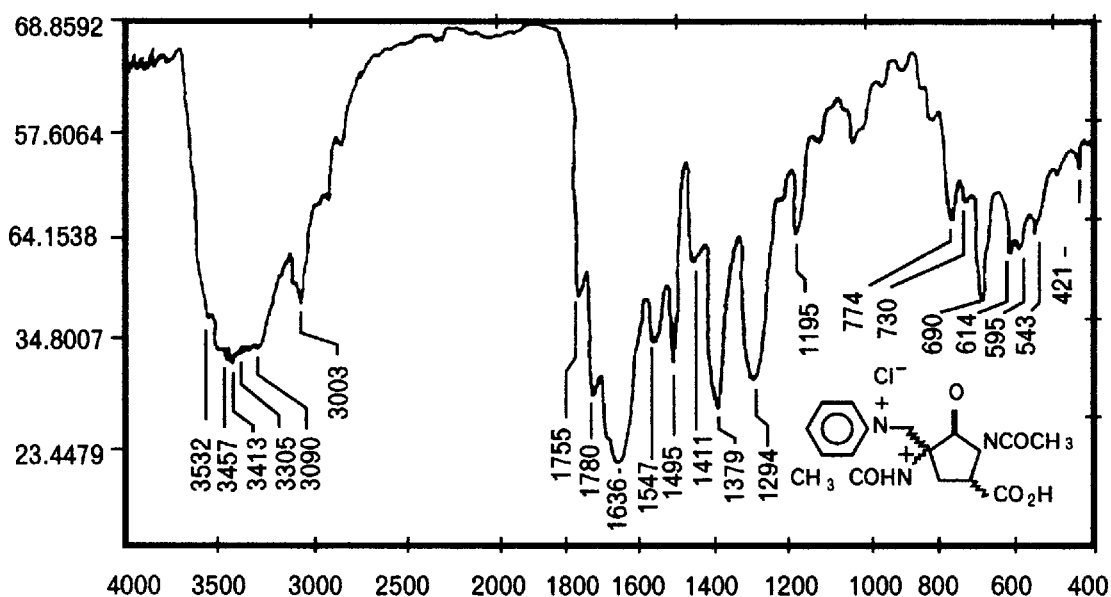
FIG. 9.—It shows the EM spectrum of the BRM-BLAS 320 (Ac) compounds.
Figure 9:
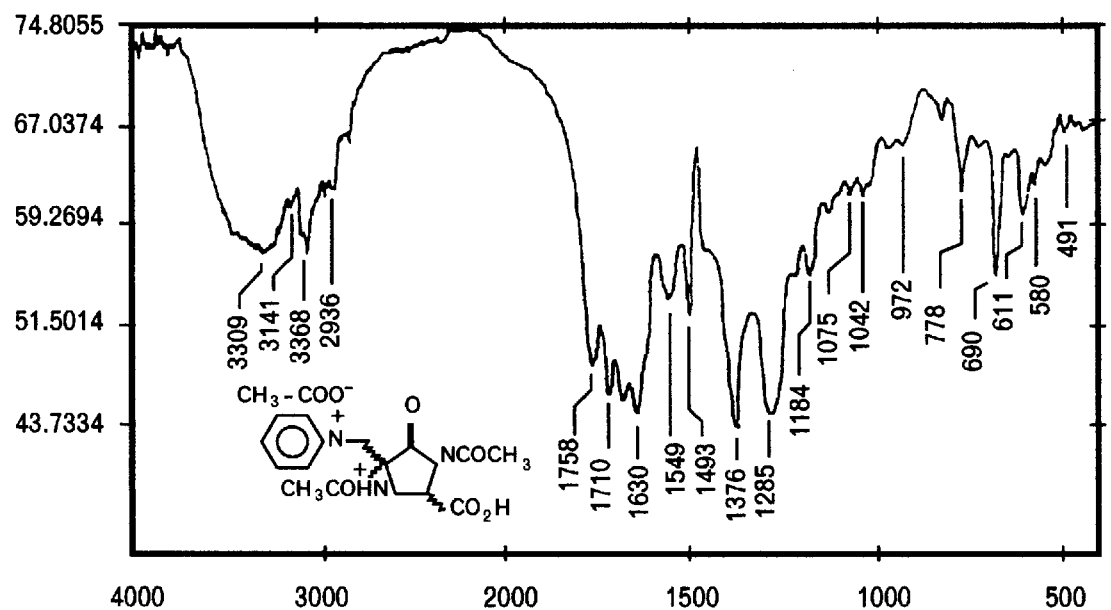
Figure 10:
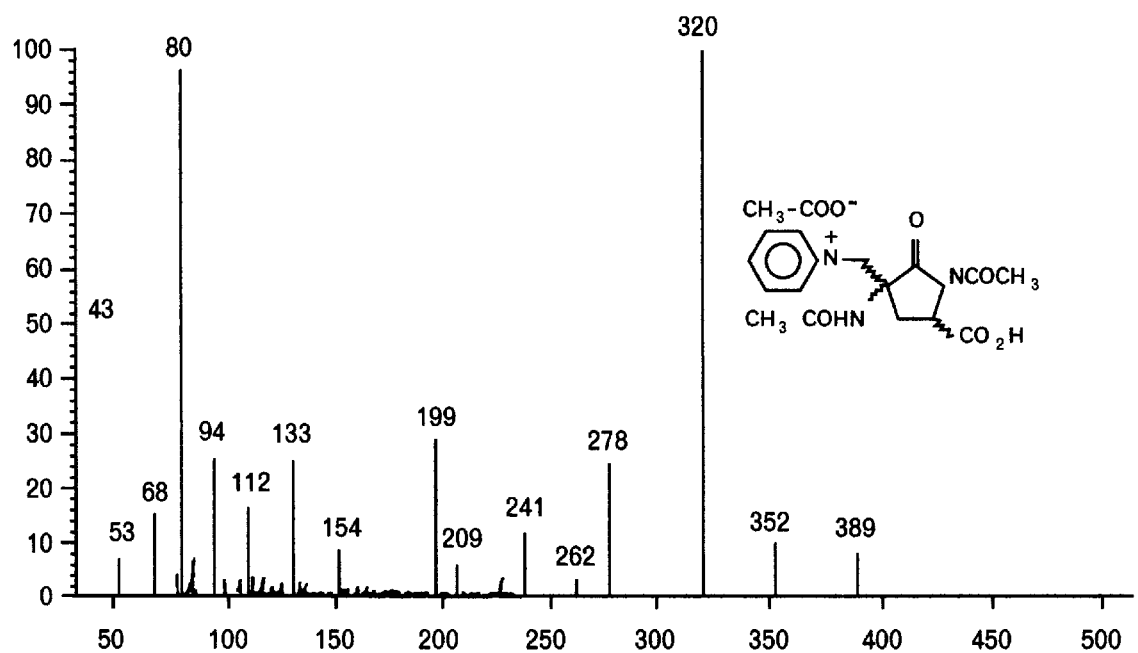
FIG. 10.—It shows the IR spectrum of the BRM-BLAS 320 (Cl) and BRM-BLAS 320 (Ac) compounds.

The EM mass spectrum of shows multiple interrelated molecular fragments that, once again, confirm the presence of the pyridine ring and the acetyl residues as an integral part of the molecular structure of such compounds (Table III and FIG. 9). The IR spectrum shows the intense (strong) bands which are a characteristic of the carbonyl groups, between 1750–1600 cm$^{-1}$ and the band II in solid phase (a combination of N—C tension and N—H flection) of the amides $R_1$—CO—NH—$R_2$ at 1547–1549 cm$^{-1}$ (FIG. 10) absent in the monoacetylated and disacetylated compounds (Table I).

EXAMPLE NO. 6

BRM-BLAS 320 (Cl)

Under this name the diacetylated derivatives of the BRM-BLAS 236 (Cl), described above, are included. They are called "1-(3-acetyl-1-acetylamino-3-aza-4-carboxy-2-oxycyclopentyl) methyl]pyridinium chloride" or "1-acetyl-4-acetylamino-4-(1-pyridiniomethyl) pyroglutamic acid chloride", the molecular formula being $C_{15}H_{18}ClN_3O_5$. In an aqueous solution they present a maximum UV absorption peak at 260 nm and they follow the Lambert-Beer law for concentrations between 10–100 micrograms/ml.

They can be indistinctly obtained from the crude product or from the BRM-BLAS 320 (Ac) compounds by treating them with a 0.05 N solution of hydrochloric acid, at room temperature, during a few minutes. The performance when the BRM-BLAS 320 (Ac) compounds are used is optimal (90%) If the Crude Product is used for the reaction of the molecular anion exchange, the product is recovered from the chromatographic column mainly in the lipophilic phase eluate. The molecular structure or the structural formula of these compounds is represented in the formula (VII).

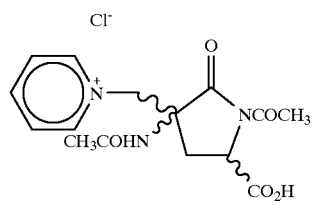

Figure 11:
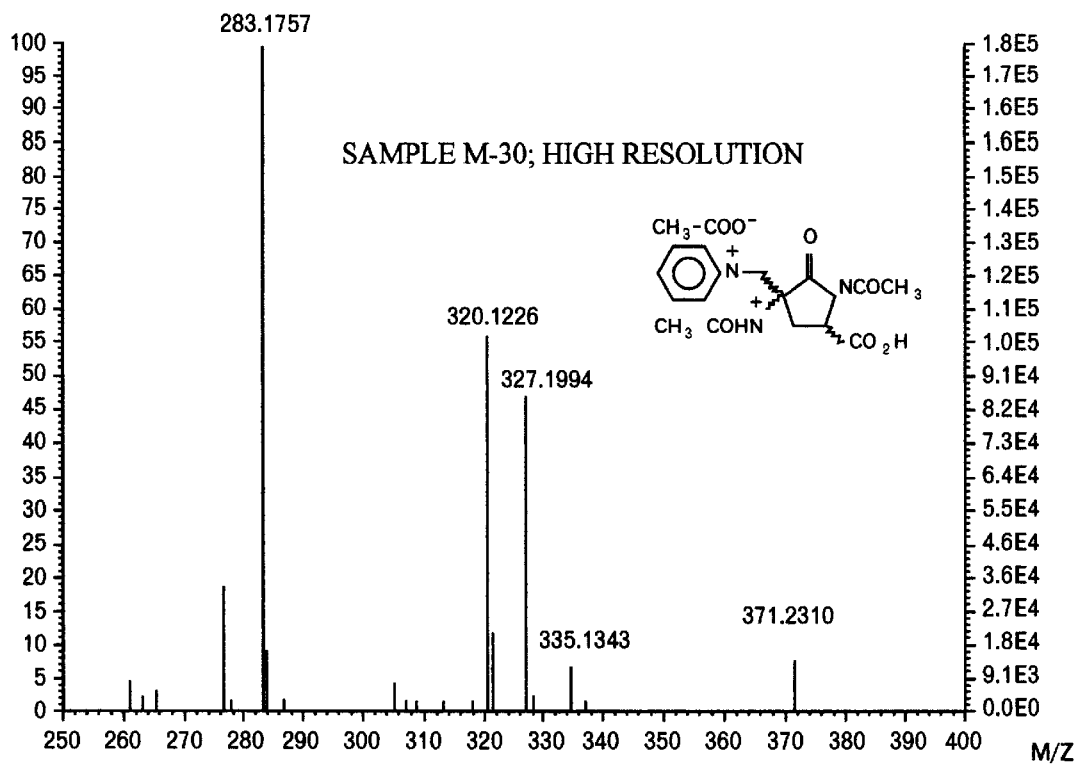
FIG. 11.—It shows the EMAR spectrum of the BRM-BLAS 320 (Ac) compounds.
Figure 11:
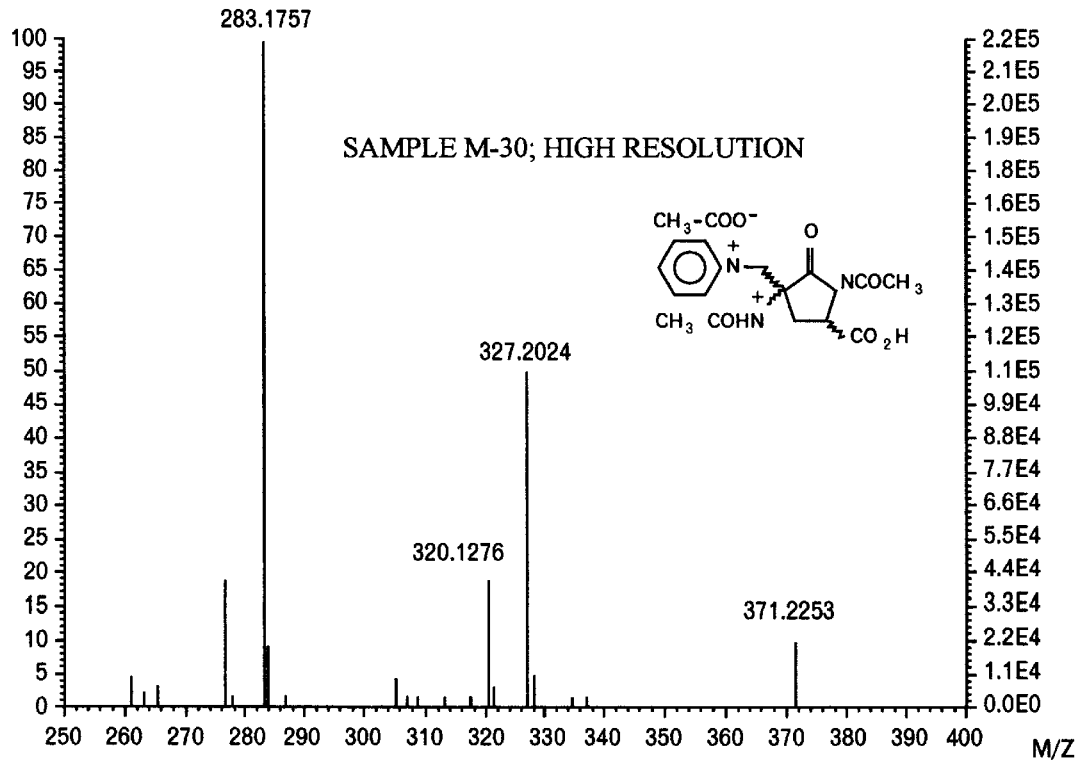

The spectroscopic data of the BRM-BLAS 320 (Cl) compounds are completely similar to those of the BRM-BLAS 320 (Ac) which they come from, with the exception of the signals corresponding to their molecular acetate anion. The IR spectrum is practically identical for the compounds of both products, (Table I) and the same can be said in the case of the EM spectrum and those of the EMARs, (FIG. 11), since the exact mass found in both cases is practically identical, 320, 12465 and 320, 12480 for the compounds with the acetate and chloride anion, respectively; exact theoretical mass calculated for the molecular formula interred, 320, 12465.

EXAMPLE NO. 7

Procedure 50 g of L-serine, 200 ml of acetate anhydride and 60 ml of pyridine were reacted at 85° C. during 25 minutes and 40 g of the crude product powder were obtained.

Preclinical Studies

The preclinical study on the lymphocyte Response and Kinetics reveals a marked immunomodulator effect of the above-mentioned BRM-BLAS compounds, which inoculation to normal individuals is perfectly tolerated and followed by a significative increase of the biological response, above the mean physiological baseline of the group.

A.—"In Vitro" Tests

The "in vitro" lymphocyte response has been assessed in samples of circulating and peripheral venous blood from asymptomatic blood donor adults of both sexes. In general, the lymphocyte cultures include in each case six experimental models called witnesses, and incorporate progressive doses between 0.25–6.0 units (20–500 ng) of the BRM-BLAS compounds and PHA. The RLP-I of each one has been morphologically determined and is expressed in absolute values of lymphoblasts/10,000.

Systematically, in all the cases it has been tabulated the RLP-I to the PHA, basal, of the PHA models; to the PHA+BRM-BLAS, of the "witness" models and the maximum individual response of the witness models (RMC), in each case. The distribution of the sample is shown in Table IV.

TABLE IV

| DISTRIBUTION OF THE SAMPLE | | | | | | |
|---|---|---|---|---|---|---|
| | GROUPS CONSIDERED - BRM | | | | | |
| | BLAS - 236 | | BLAS - 278 | | BLAS - 320 | |
| TESTS | (Cl) | (Ac) | (Cl) | (Ac) | (Cl) | (Ac) | TOTAL |
| Number of cases | 11 | 15 | 16 | 9 | 16 | 14 | 81 |
| PHA Model alone | 11 | 15 | 16 | 9 | 16 | 14 | 81 |
| PHA + BRM-BLAS | 66 | 90 | 93 | 54 | 96 | 82 | 481 |
| TOTAL TESTS | 77 | 115 | 109 | 63 | 112 | 96 | 562 |

77% of the witness models globally show a RLP-I super-added to that of the respective basal PHA which varies among the groups from 70% [BRM-BLAS 236 (Cl) and BRM-BLAS 320 (Cl)] to 83% [BRM-BLAS 278 (Cl)], Table V.

TABLE V

| INTERMODEL GLOBAL ANALYSIS | | | | | | | |
|---|---|---|---|---|---|---|---|
| EXPERIMENTAL | GROUPS CONSIDERED - BRM | | | | | | |
| MODEL | BLAS - 236 | | BLAS - 278 | | BLAS - 320 | | TOTAL |
| PHA (A) VERSUS PHA + BRM-BLAS (B) | (Cl) Num. (%) | (Ac) Num. (%) | (Cl) Num. (%) | (Ac) Num. (%) | (Cl) Num. (%) | (Ac) Num. (%) | CASOS Num. (%) |
| RLP-I B > A | 46(70) | 73(81) | 77(83) | 40(74) | 67(70) | 65(70) | 368(77) |
| RLP-I B < A | 20(30) | 17(19) | 16(17) | 14(26) | 29(30) | 17(21) | 113(23) |
| TOTAL | 66(100) | 90(100) | 93(100) | 54(100) | 96(100) | 82(100) | 481(100) |

The intragroup individual analysis reveals, in turn, that the RLP-I to the PHA, basal, is exceeded in all cases, at least by 33%–50% of the respective witness models; in 74% by 67% of them, and in 30% by all, Table VI. These response patterns discard any randomized results and fully confirmed the cause-effect relation between the incorporation of BRM-BLAS compounds to the witness models and the RLP-I super-added to that of their PHA, basal.

TABLE VI

INTRAGROUP RLP-1 INTERMODEL INDIVIDUAL ANALYSIS

| EXPERIMENTAL MODELS | GROUPS CONSIDERED - BRM | | | | | | |
|---|---|---|---|---|---|---|---|
| | BLAS - 236 | | BLAS - 278 | | BLAS - 320 | | TOTAL |
| PHA (A) VERSUS PHA + BRM-BLAS (B) | (Cl) Num. (%) | (Ac) Num. (%) | (Cl) Num. (%) | (Ac) Num. (%) | (Cl) Num. (%) | (Ac) Num. (%) | CASOS Num. (%) |
| RLP-I B > A(33–50%)# | 11(100) | 15(100) | 16(100) | 9(100) | 16(100) | 14(100) | 81(100) |
| RLP-I B > A(67%)# | 9(82) | 12(82) | 13(81) | 6(67) | 11(69) | 9(64) | 60(74) |
| RLP-I B > A(100%)# | 2(18) | 6(40) | 6(37) | 3(33) | 2(13) | 5(36) | 24(30) |

%: Percentage of the witness models with a RLP-I B > A

The statistical assessment of the groups is also concluding. The RLP-I mean of each witness model of the group, irrespective of the relevant BRM-BLAS dose, exceeds that of the respective basal PHA (Table VII). Such response depends on the dose and the maximum values of the mean are distributed among the witness models with the higher experimental doses, corresponding 50%, 33% and 17% of such values to the models with three (210 ng), six (420 ng) and two units (140 ng) respectively (Table VII). The RLP-I super-added to that of the basal PHA of the group is statistically significant in 81% of the witness models and exceeds one standard deviation in 36% of them.

However, the most representative measure or indicator of the potential immunomodulating activity of such compounds could probably be the RMC individual or that of the group, which finally would be conditioned by the (limited) number of witness models. In this context, the intragroup values of the individual RMC reveal in most cases (50%–60%) a very significant increase of the RLP-I super-added to that of the respective basal PHA (100%) that oscillate within groups from 167% to 227% [BRM-BLAS 278 (Ac)] and from 191% to 298% [BRM-BLAS 320 (Ac)]. The highest mean of the groups prepared on the basis of the RMC individual represents a statistically and biologically significant increase, of the RLP-I super-added to that of the PHA, which in 83% is higher than two or three standard deviations, Table VII.

TABLE VII

"IN VITRO" RLP-I ADDED TO THAT OF THE PHA STATISTICAL ASSESSMENT

GROUPS CONSIDERED

| EXPERIMENTAL MODELS (PHA + BRM-BLAS) | BRM - BLAS - 236 | | | | | | | | | |
|---|---|---|---|---|---|---|---|---|---|---|
| | (Cl) | | | | | (As) | | | | |
| | MD | # | SX | # | % | # | MD | # | SX | # | % | # |
| 0.12 ml + 0.00 u | 88 | | 25 | | 100 | | 86 | | 30 | | 100 | |
| 0.12 ml + 0.25 u | 103 | | 35 | | 117 | | 109 | ■ | 32 | | 127 | |
| 0.12 ml + 0.50 u | 111 | | 36 | | 126 | | 104 | | 36 | | 121 | |
| 0.12 ml + 1.00 u | 121 | ▩ | 28 | 1 | 126 | 1 | 101 | | 35 | | 117 | |
| 0.12 ml + 2.00 u | 127 | | 52 | 1 | 144 | 1 | 104 | | 33 | | 121 | |
| 0.12 ml + 3.00 u | 134 | ▩ | 46 | 1 | 152 | 1 | 128 | | 53 | 1 | 149 | 1 |
| 0.12 ml + 6.00 u | 119 | | 39 | | 135 | | 106 | | 40 | 1 | 126 | 1 |
| RMC | 168 | ■ | 39 | 3 | 191 | 3 | 146 | ■ | 45 | 2 | 170 | 2 |

TABLE VII-continued

"IN VITRO" RLP-I ADDED TO THAT OF THE PHA STATISTICAL ASSESSMENT

GROUPS CONSIDERED

| EXPERIMENTAL MODELS (PHA + BRM-BLAS) | BRM - BLAS - 278 | | | | | | | | | | | |
|---|---|---|---|---|---|---|---|---|---|---|---|---|
| | (Cl) | | | | | | (As) | | | | | |
| | MD | # | SX | # | % | # | MD | # | SX | # | % | # |
| 0.12 ml + 0.00 u | 88 | | 28 | 1 | 100 | 1 | 87 | | 32 | | 100 | |
| 0.12 ml + 0.25 u | 118 | | 38 | | 135 | | 96 | | 26 | | 110 | |
| 0.12 ml + 0.50 u | 109 | ■ | 43 | | 127 | | 97 | | 36 | | 111 | |
| 0.12 ml + 1.00 u | 108 | | 39 | | 126 | | 107 | | 34 | | 123 | |
| 0.12 ml + 2.00 u | 115 | | 55 | 1 | 134 | 1 | 110 | | 34 | | 126 | |
| 0.12 ml + 3.00 u | 124 | ▩ | 53 | 1 | 145 | 1 | 103 | | 38 | | 118 | |
| 0.12 ml + 6.00 u | 108 | | 55 | | 126 | | 127 | ■ | 41 | 1 | 146 | 1 |
| RMC | 158 | ■ | 48 | 3 | 184 | 3 | 142 | ■ | 27 | 1 | 163 | 1 |

| EXPERIMENTAL MODELS (PHA + BRM-BLAS) | BRM - BLAS - 320 | | | | | | | | | | | |
|---|---|---|---|---|---|---|---|---|---|---|---|---|
| | (Cl) | | | | | | (As) | | | | | |
| | MD | # | SX | # | % | # | MD | # | SX | # | % | # |
| 0.12 ml + 0.00 u | 106 | | 28 | | 100 | | 75 | | 25 | | 100 | |
| 0.12 ml + 0.25 u | 130 | | 43 | | 123 | | 93 | ▩ | 23 | | 124 | |
| 0.12 ml + 0.50 u | 132 | | 50 | | 125 | | 99 | | 50 | | 132 | |
| 0.12 ml + 1.00 u | 125 | ▩ | 34 | | 118 | | 96 | | 30 | | 128 | |
| 0.12 ml + 2.00 u | 138 | ▩ | 43 | 1 | 130 | 1 | 94 | | 49 | | 125 | |
| 0.12 ml + 3.00 u | 136 | ▩ | 41 | 1 | 128 | 1 | 96 | ▩ | 42 | | 128 | |
| 0.12 ml + 6.00 u | 120 | | 51 | | 113 | | 108 | ■ | 36 | 1 | 144 | 1 |
| RMC | 185 | ■ | 44 | 3 | 175 | 3 | 144 | ■ | 43 | 3 | 192 | 3 |

MD represents the average of the total number of lymphoblasts/10.000
(%) > 15X = 1
(%) > 25X = 2
(%) > 35X = 3
MD ($P < 0.05$) =
MD ($P < 0.01$) = ▩
MD ($P < 0.001$) = ■

B. "In Vivo" Tests

The pharmacodynamic study to assess the leuko-lymphocyte kinetics has been carried out in New Zealand's albino, giant, female, adult, asymptomatic (healthy) rabbits. The blood samples with EDTA (ethylene-diamino-tetraAcetic acid), non-coagulable, for the periodical weekly controls, have been obtained by aseptic puncture from the marginal vein of the outer ear. The count and the differential cytologic survey of the white series has been routinely performed in a "Coulter" (Coulter Científica, S.A., STKs model) differential analyzer, within the two hours following the extraction.

Hereinafter, there is a summary of the most significant results of the preclinical protocols which include different experimental conditions, different BRM-BLAS products and doses which vary in vary of their concentration of the product, frequency and number.

I. Successive Doses (BRM-BLAS 236 (Cl))

Figure 12:
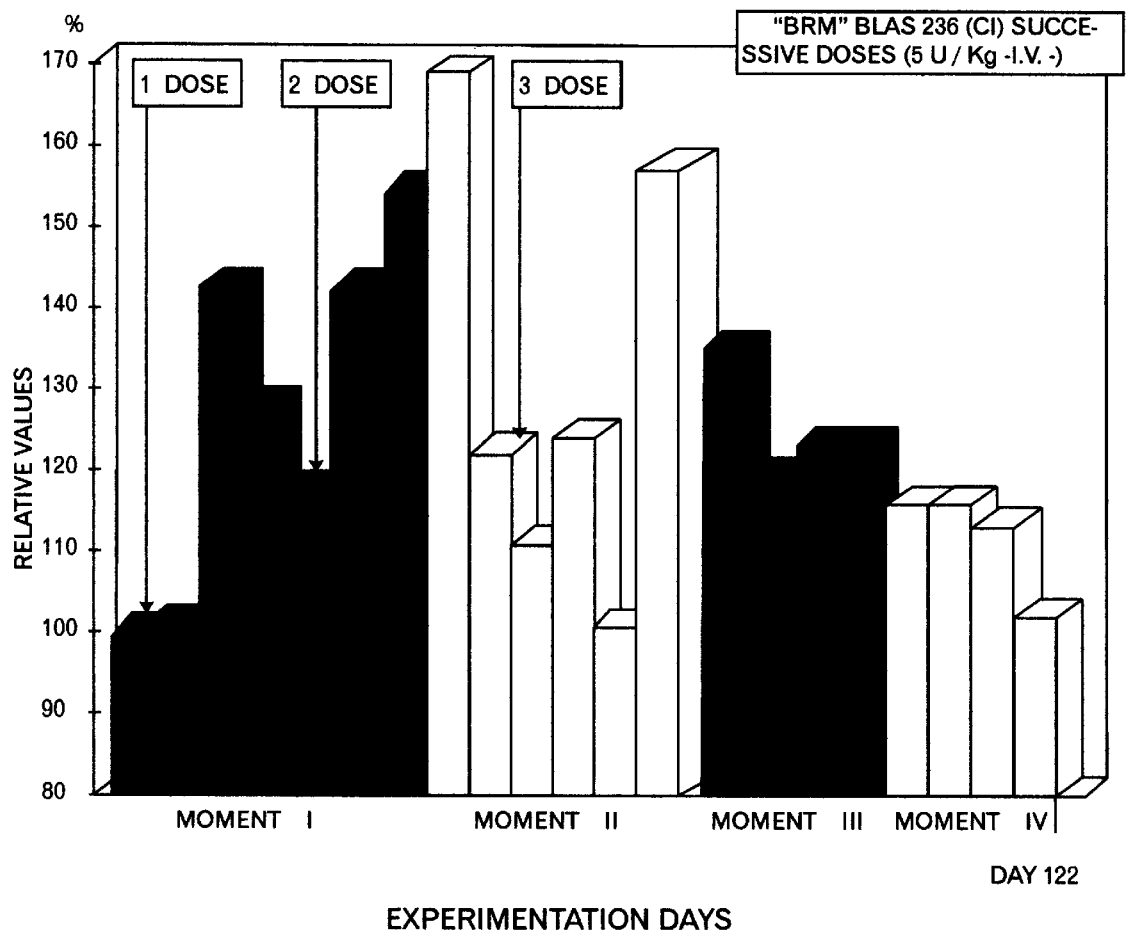
FIG. 12.—It shows the graphs corresponding to the leukocyte kinetics after the immunomodulation with BRM-BLAS 236 (Cl) compounds.
Figure 13:
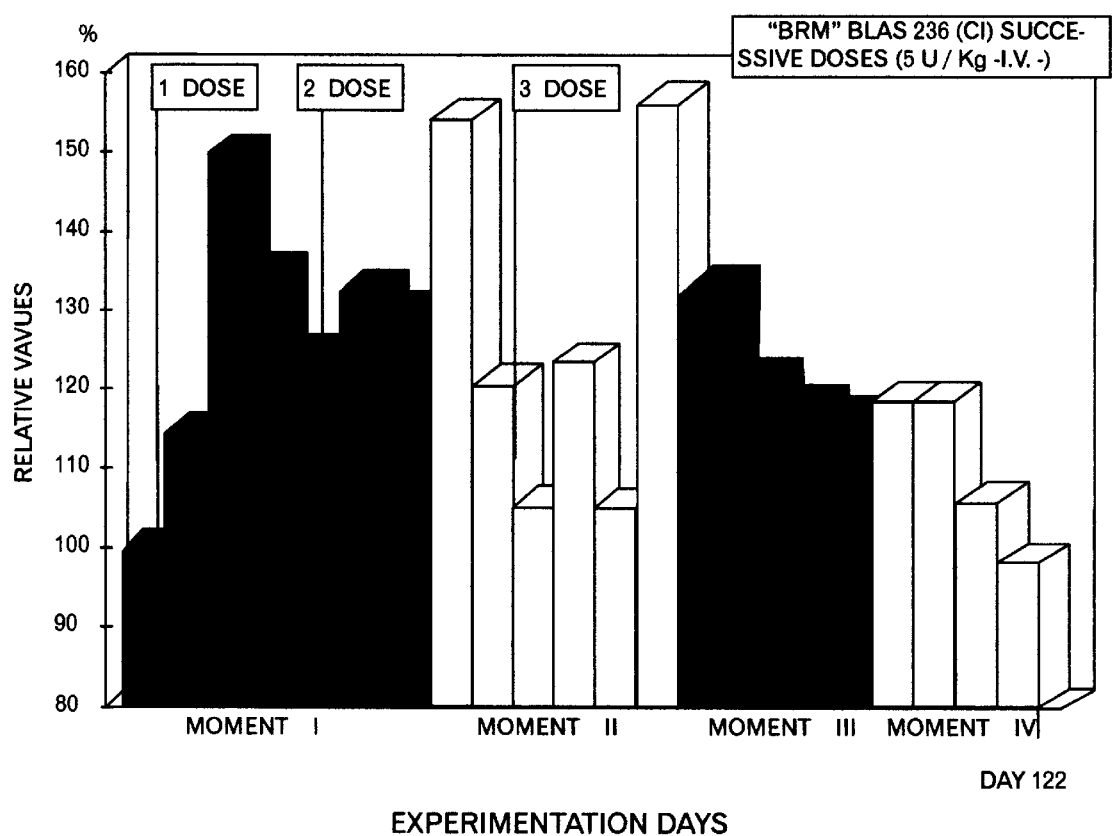
FIG. 13.—It shows the graphs corresponding to the lymphocyte kinetics after the immunomodulation with BRM-BLAS 236 (Cl) compounds.

The administration every 21 days of three successive intravenous doses of the BRM-BLAS 236 (Cl) compounds, each one of 5 U/Kg (300 ng/Kg) to 3-year old asymptomatic rabbits, without any other immunomodulating treatment during the previous months, was followed in all cases by an increase in the number of leukocytes which affect granulocytes as well as lymphocytes in the same way. The leuko-lymphocyte mean values of the group run parallelly during the study, in general above the respective basal values before the treatment to which they return in the last two assessments. They reach the higher ones 7, 16 and 20 days after the first, second and third dose, FIG. 12, FIG. 13 and Table VIII (assessments: 3, 8 and 13).

Statistically, the leukocyte (FIG. 12) and lymphocyte (FIG. 13) mean values of the group exceed the basal ones over the standard deviation in 55% and 75% of the assessments; by more than two in 20%, and an by more than three in 5% and 10% respectively. Furthermore the difference between them is statistically significant, in 70% of the assessments in the case of the leukocytes and in 35% in the case of the lymphocytes. Their highest values correspond to the assessment 8 of the study (37th day) and represent an increase over the basal ones of 169% and 157% respectively. Once the results have been grouped, the difference between the leuko-lymphocyte mean values of the "first" period (3rd to 31st Day; 24 assessments) and the "second" period (37th to 64th day; 24 assessments) during the treatment versus those of the "third" period (71st to 92nd day; 16 assessments) and "fourth" period (102nd to 122nd day; 16 assessments) post-treatment, is statistically significantly surpassing the mean values of the "first" period exceed those of the "fourth" period and the basal ones, practically by two standard deviations, Table VIII.

individual assessments (8 of the group) after the two first doses, days 0 to 43rd; the "second", the 85 (17 of the group) after the third, fourth and fifth doses, days 46th to 147th; the "third", the first 50 (10 of the group) after the sixth, days 153rd to 213th, and the "fourth", the last 50 (10 of the group), days 220th to 282nd, respectively. The assessment of the group prior to the third dose (43rd day), the lymphocyte mean of which has been the lowest during the survey, has been taken as the natural reference baseline for the comparative analysis of punctual and grouped data.

Logically, the lymphocyte mean of the group in all the assessments exceeds the selected basal (100%). However, there are large variations among the moments under consideration. In the "first" one, the relative values of such mean in each assessment oscillate from 103% to 117% of the basal, and in all of them the difference is lower than one standard deviation. In the "second" one, the values vary from 108% to 141% of the basals, 41% exceed one standard deviation and 43% reveal a statisitically significant difference. In the "third" and "fourth", the response is statistically and biologically more significant (Table IX). 80% of the assessment of the group in the "third" one and 100% in the "fourth" one exceed the mean of the lymphocyte basal values by more than one, two or three standard deviations and in all of them the difference is statistically significant. The highest average values reach a 178% over the basal values on the 92nd day after the sixth dose (day 241st of the study) "fourth" moment, FIG. 14.

Figure 15:
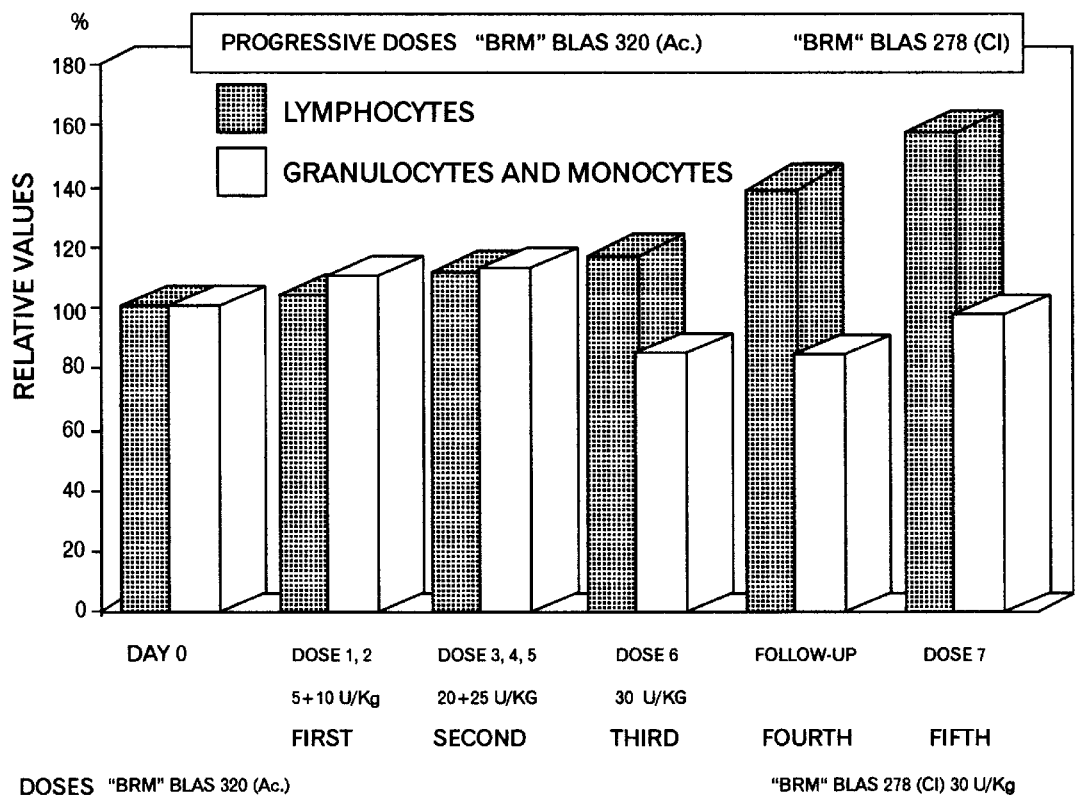
FIG. 15.—It shows the graphs corresponding to the leuko-lymphocyte response after the immunomodulation with BRM-BLAS 320 (Ac) and 278 (Cl) compounds.

The lymphocyte mean of the group, obtained from the results grouped in the four evolutive periods described above, increases from the baseline, in a progressive and uninterrupted way, from 110% on the "first" one to 120% on the "second", 131% on the "third" and 152% on the "fourth" (FIG. 15). The difference between the mean values of such groupings is statistically significant and that of the "fourth" moment exceeds that of the "first" one by more than one standard deviation. Moreover, the difference between the

TABLE VIII

LEUKO-LYMPHOCYTE KINETICS AFTER THE IMMUNOMODULATION
SUCCESSIVE DOSES OF BRM-BLAS 236 (Cl) 5 U/Kg - I.V.
Significance Levels - "p" Values

| | EXPERIMENTAL TIMES ||||||||||
| EXPERIMENT- | LEUKOCYTES ||||| LYMPHOCYTES |||||
| AL TIMES | BASAL | FIRST | SECOND | THIRD | FOURTH | BASAL | FIRST | SECOND | THIRD | FOURTH |
|---|---|---|---|---|---|---|---|---|---|---|
| BASAL  | #### | 0.050 | 0.050 | 0.100 | 0.400 | #### | 0.010 | 0.050 | 0.100 | 0.400 |
| FIRST  | 0.050 | #### | 0.900 | 0.500 | 0.050 | 0.010 | #### | 0.800 | 0.400 | 0.050 |
| SECOND | 0.050 | 0.900 | #### | 0.600 | 0.100 | 0.050 | 0.800 | #### | 0.700 | 0.400 |
| THIRD  | 0.100 | 0.500 | 0.600 | #### | 0.200 | 0.100 | 0.400 | 0.700 | #### | 0.300 |
| FOURTH | 0.400 | 0.050 | 0.100 | 0.200 | #### | 0.400 | 0.050 | 0.400 | 0.300 | #### |

Probability levels from the "Statistical tables for Biological, Medical and Agricultural Research, Fisher & Yates, Bdienburgh, Oliver and Lloyd, Liod. 1931"

II. Progressive Doses (BRM-BLAS 320 (Ac))

Figure 14:
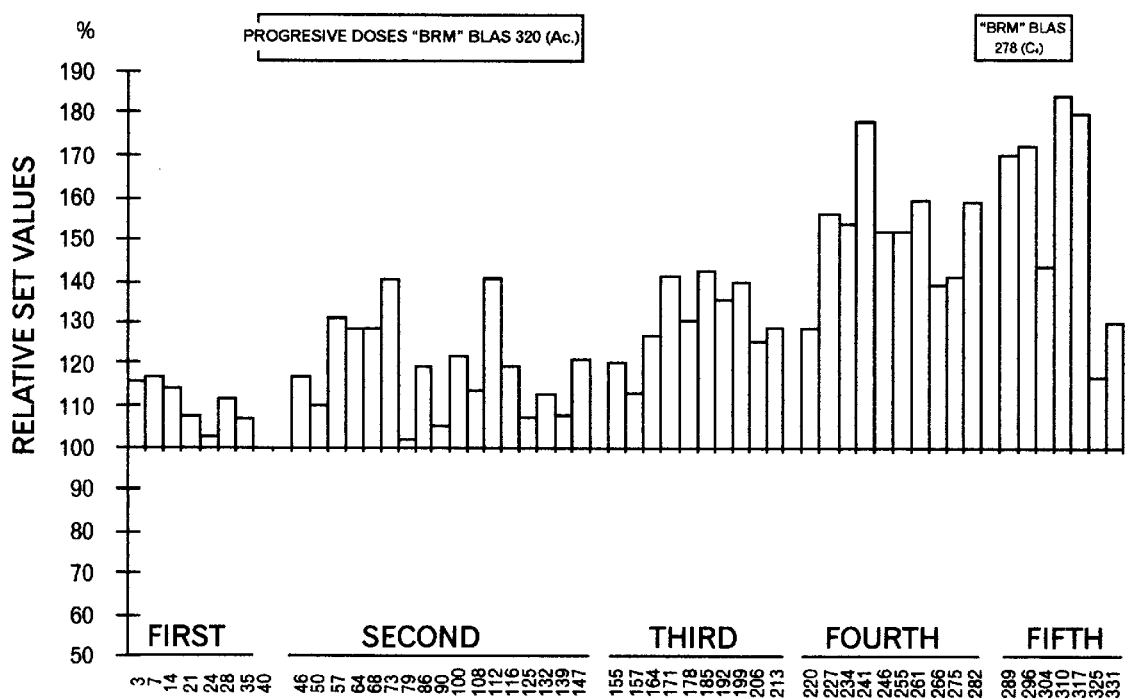
FIG. 14.—It shows the graphs corresponding to the lymphocyte response after the immunomodulation with BRM-BLAS 320 (Ac) and 278 (Cl) compounds.

The intravenous administration of the BRM-BLAS 320 (Ac) compounds in progressive doses of 5, 10, 15, 20, 25 and 30 units/Kg (0.4–2.4 mcg/Kg), the days 0, 21st, 43rd, 64th, 109th and 153rd of the survey to 3½ year old asymptomatic rabbits and without any other immunomodulating treatment during the months prior to the first dose, was followed in all cases by a selective and significant increase in the number of lymphocytes that starts after the third dose and reaches its maximum level after the sixth, FIG. 14 and Table IX.

A total number of 225 individual assessments and 45 of the group assessments have been performed, grouped in four evolutive periods moments. The "first" one includes the 40 individual lymphocyte mean of each animal of the group at the "fourth" moment versus the "first" is statistically significant and higher in two or three standard deviations in 40% and 60% of the animals, respectively.

Paradoxically, the leukocyte mean values of punctual assessments of the group exceeds by one standard deviation of the basal values only in two occasions (4.4%), 227$^{th}$, (129%) and 241st (136%) day and during the study the difference is never became statistically significant. However, the group mean obtained from the data gathered shows differences that are statistically significant between the "fourth" versus the "first" or "third" moment and the "second" versus the "third" one but it never exceeds one standard deviation (Table IX). Finally, two animals (40%), individually, exceed at the "fourth" moment the respective figures of the mean values in the "first" one by two or three standard deviations, and the difference is statistically significant in both cases.

of BRM-BLAS 236 (Cl) compounds and includes 30 individual assessments (6 of the group) days 0 to 39. The second "second" moment, is centered on the successive changes occurred after the administration on the 39th day of an

TABLE IX

LEUKO-LYMPHOCYTE KINETICS AFTER THE IMMUNOMODULATION
Significance Levels - "p" Values

| EXPERIMENTAL TIMES | LEUKOCYTES | | | | | LYMPHOCYTES | | | | |
|---|---|---|---|---|---|---|---|---|---|---|
| | FIRST | SECOND | THIRD | FOURTH | FIFTH | FIRST | SECOND | THIRD | FOURTH | FIFTH |
| "BRM" BLAS 320 (Ac) | | | | | | | | | | |
| FIRST | #### | 0.2420 | 0.1840 | 0.0179 | 0.0050 | #### | 0.0359 | 0.0001 | 0.0001 | 0.0001 |
| SECOND | 0.2420 | #### | 0.0446 | 0.0970 | 0.0228 | 0.0359 | #### | 0.0359 | 0.0001 | 0.0001 |
| THIRD | 0.1840 | 0.0446 | #### | 0.0190 | 0.0002 | 0.0001 | 0.0359 | #### | 0.0026 | 0.0035 |
| FOURTH | 0.0179 | 0.0970 | 0.0190 | #### | 0.2420 | 0.0001 | 0.0001 | 0.0026 | #### | 0.3446 |
| "BRM" BLAS 278 (Cl) Subcutaneous | | | | | | | | | | |
| FIFTH | 0.0050 | 0.0228 | 0.0002 | 0.2420 | #### | 0.0001 | 0.0001 | 0.0035 | 0.3446 | #### |

(*) Probability levels from the "Introduction to biostatistics"; Libers & (HULDAH BANCROFT); Page 72, table XIV III. Unique Dose, High (BRM-BLAS 278 (Cl))

This trail is subsequent to the protocol previously described and corresponds to the "fifth" moment of the global study, FIG. 14 and FIG. 15.

After the subcutaneous administration of a dose of 30 u/Kg (2.1 mcg/Kg) of the BRM-BLAS 278 (Cl) compounds 137 days after the sixth dose of the BRM-BLAS 320 (Ac) compounds, in the presence of high figures of the lymphocyte mean of the group, at the "fourth" moment, such figures were specifically exceeded by the 4th and 5th punctual weekly assessments of the "fifth" moment, 24th (184%) and 31st (180%) days, respectively, FIG. 14. Globally, 28% of the assessment exceed basal values by one or two standard deviations; 57% in three, and the difference is statistically in all of them. The resulting mean of the data gathered for the "fifth" moment with a 158% of the basal values, exceed those of the four previous moments, and the difference is statistically significant compared with those of the "first", "second" and "third", and exceeds that of the "first" in more than one standard deviation, FIG. 15 and (Table IX).

Individually, the difference between the lymphocyte mean values of each one of the animals at the "fifth" moment versus the "first" one is statistically significant and higher than two or three standard deviations in 20% and 80% of the animals, respectively.

The leukocyte mean of 57% of the routine weekly assessments of the group exceeds the basal figures by one standard deviation and the difference is statistically significant in 29%.

The leukocyte mean of the group resulting from the data collected at the "fifth" moment shows statistically significant differences when compared with the "first", "second" and "third" moments which in all cases, is lower than one standard deviation (Table IX). Finally, and on individual basis, the mean at the "first" moment of 40% of the animals is exceeded at the "fifth" moment by more than two standard deviations and the difference between them is statistically significant.

IV. Single Low Dose, Versus Single High Dose, BRM-BLAS 278 (Ac) and BRM-BLAS 320 (Ac), Respectively This study comprises three concatenated experimental situations. The first one is focused on the vicissitudes of the leuko-lymphocyte kinetics occurred during a pause, "first" moment, that takes place months after several doses, mainly intravenous dose of 8 u/Kg (0.6 mcg/Kg) of the BRM-BLAS 278 (Ac) compounds and includes a total of 25 individual assessments (5 of the group), days 43rd to 68th. The third one, moments "third" to "seventh", analyzes the changes induced after the intravenous administration on the 68th day of 22 u/Kg (1.8 mcg/Kg) of BRM-BLAS 320 (Ac) compounds and includes 150 individual assessments (6 of the group×5 times), days 75th to 287th of the study. The assessment prior to the last dose, the lymphocyte average of which is the lowest of the group during the study, has been selected as the common baseline (100%) for reference of the comparative analysis between the assessments.

Regarding the mean of the lymphocyte number, the peaks of the second and fifth assessment of the first block stand out ostensibly—pause between the treatments—which due to the "weight" of an outliner reach 157% and 164% of the baseline values, respectively, but are not statistically significant. After the low dose of the BRM-BLAS 278 (Ac) compounds, second block, the group mean in the fifth assessment appears in the basal line of the histogram, after some mere fluctuations, FIG. 16.

On the contrary, twenty days after the high dose of the BRM-BLAS 320 (Ac) compounds, such mean starts a scaling which surpasses the baseline by two or three standard deviations from the 53rd day and is statistically significant uninterruptedly, until the 213th day, the end of the study. Its highest values in respect of the basal ones reach 212%, on the 88th (fourth block) and 202nd days (seventh block) after the above-mentioned dose, the precise moment at which repeatedly the maximum biological response of all animals coincided—a synchronization of the response due "a priori" to the treatment, FIG. 16.

The lymphocyte mean resulting from the grouped data of the group in the seven evolutive moments reveals differences between them that are statistically significant, specifically the "fourth", "fifth", "sixth" and "seventh" moments over the "first", "second" and "third" ones, despite the relatively limited number of their assessments (Table X). The individual mean at the "seventh" moment exceeds that of the "first" one by one, two or three standard deviations in 80% of the cases and is statistically significant in all of them.

The leukocyte mean of the group exceeds the baseline by one standard deviation in 39% of the assessments; by two, in 24%, and by three in 5% (FIG. 17), and the difference is statistically significant in 12% of them. The leukocyte mean derived from the grouped data of the group shows statistically significant differences between the "fourth" and "sixth" moments versus the "second" and "third" ones (Table X), and that never exceeds one standard deviation. On the contrary, individually, no significant differences are observed between the different experimental moments.

Figure 16:
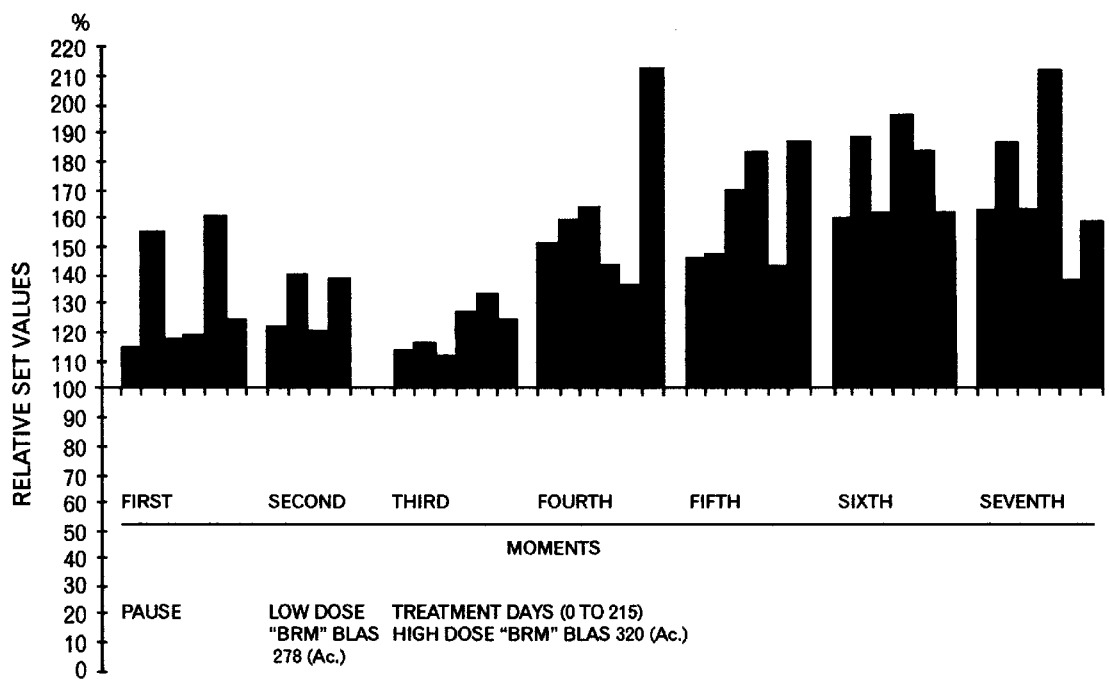
FIG. 16.—It shows the graphs corresponding to the lymphocyte kinetics after the immunomodulation with BRM-BLAS 278 (Ac) and BRM-BLAS 320 (Ac) compounds.
Figure 17:
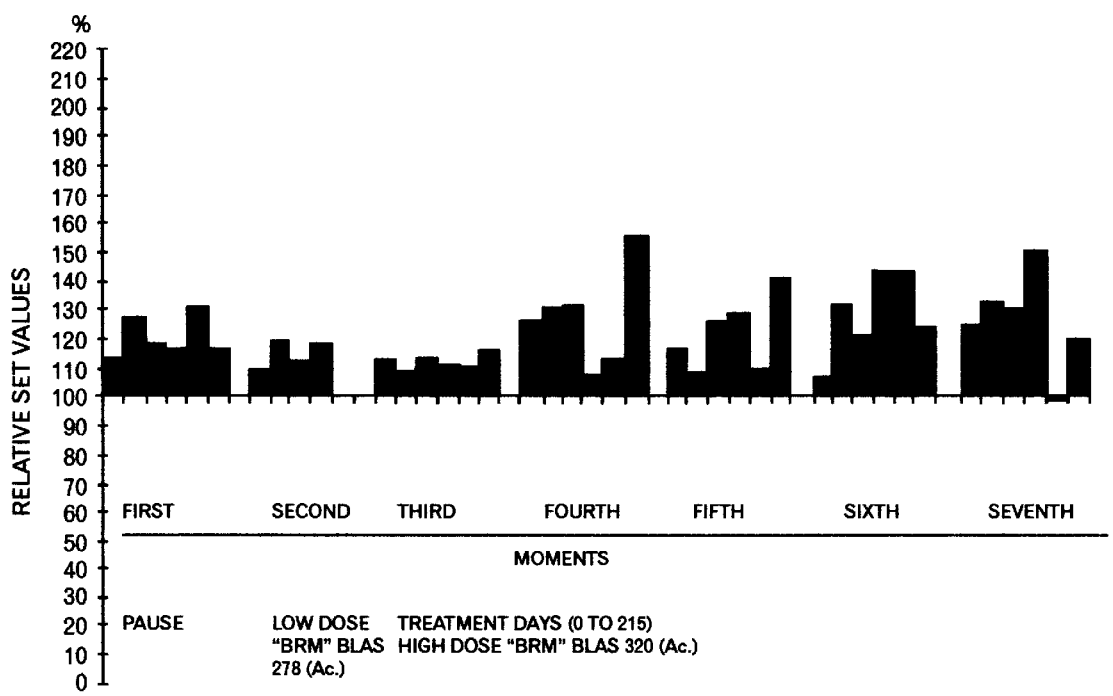
FIG. 17.—It shows the graphs corresponding to the leukocyte kinetics after the immunomodulation with BRM-BLAS 278 (Ac) and BRM-BLAS 320 (Ac) compounds.
Figure 18:
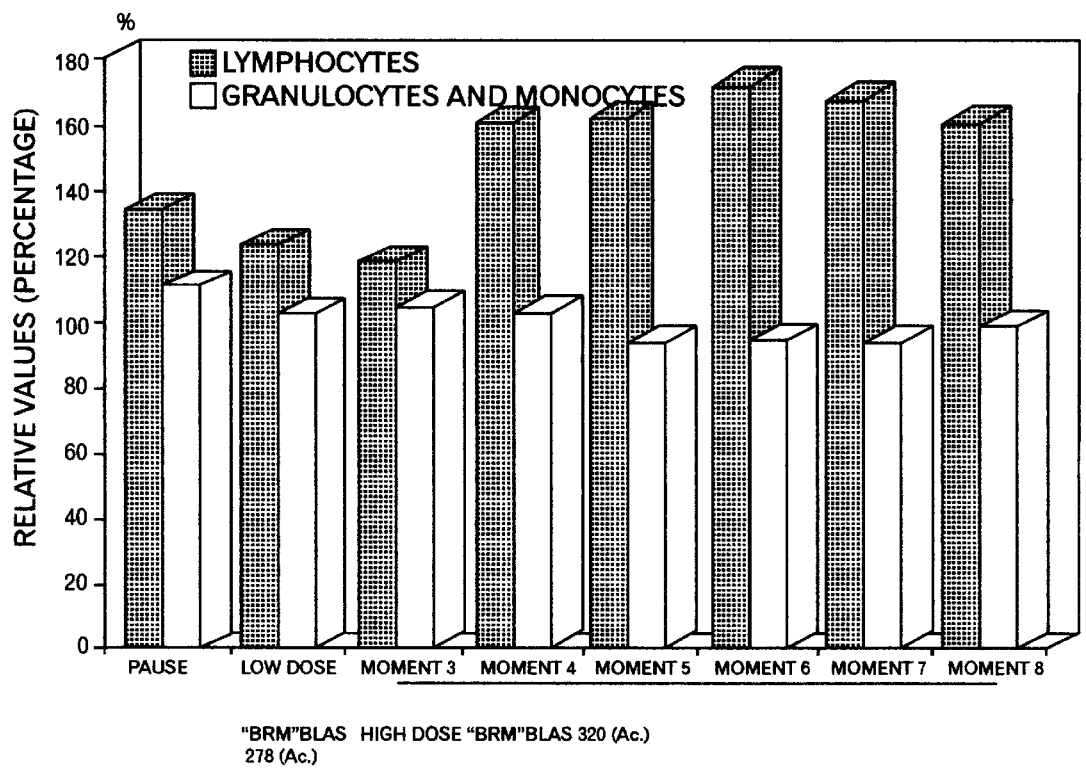
FIG. 18.—It shows the graphs corresponding to the leuko-lymphocyte response after the immunomodulation with BRM-BLAS 278 (Ac) and BRM-BLAS 320 (Ac) compounds expressed as relative values (percentages).
Figure 19:
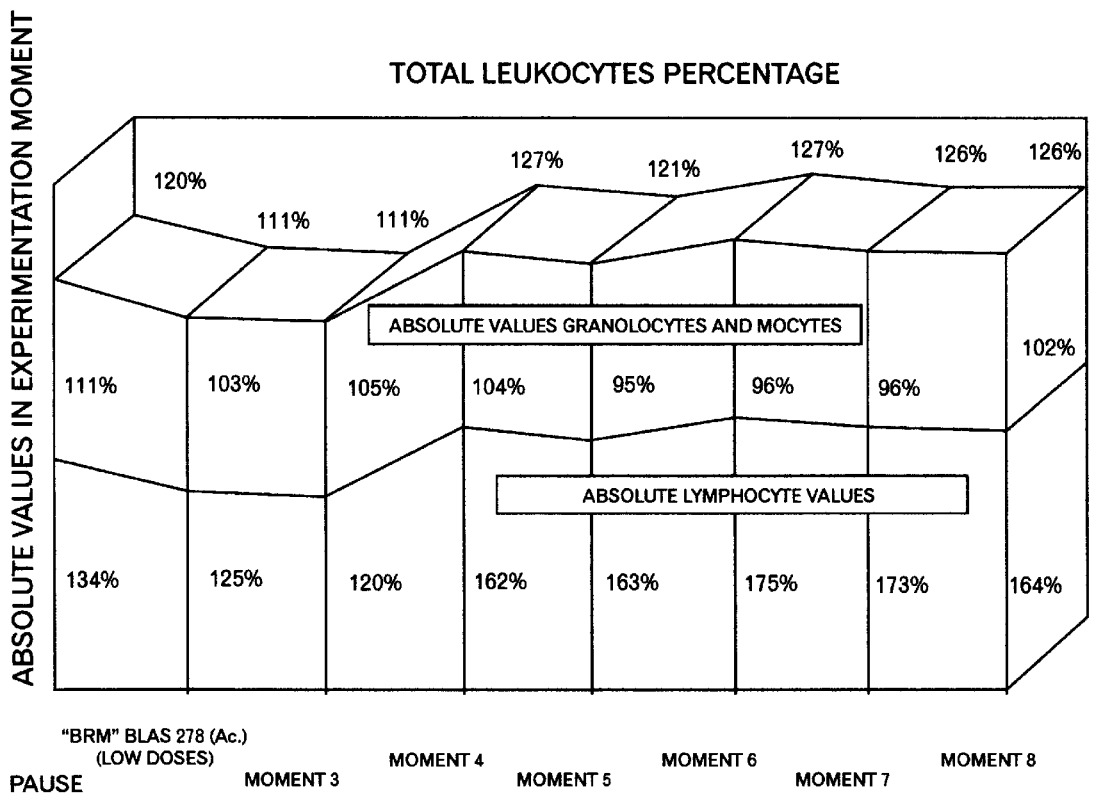
FIG. 19.—It shows the graphs corresponding to the leukocyte-lymphocyte response after the immunomodulation with BRM-BLAS 278 (Ac) and BRM-BLAS 320 (Ac) compounds expressed as absolute values.

Finally, the separated assessment of the relative and absolute figures of lymphocytes versus granulocytes and monocytes together, clearly shows a sustained and selective immunomodulating activity or effect of the BRM-BLAS 320 (Ac) compounds on subpopulations of lymphocytes without detriment to the number of granulocytes and monocytes, FIG. 18 and FIG. 19 (histograms include the 8th moment that follows the response pattern of the previous ones, FIG. 16 and FIG. 17).

The action mechanism is not known yet; however, it is assumed that the common mechanism of both "in vitro" and "in vivo" experimental models is a modulation on the cell differentiation (Ontogeny and the subsequent increase of the (absolute) number of mature and quiescent T lymphocytes (T Repertoire, available). Such subpopulations sensitive to the PHA, would be on the one hand recruited for the "in vitro" RLP-I and, on the other hand, would "in vivo" induce (peripheral) regulating signals inducing the increase in the number of circulating peripheral lymphocytes above the basal figures.

V. Toxicity

The intraperitoneal administration to Swiss, male and female, adult, healthy mice of a single dose of the BRM-BLAS 236 (Cl), BRM-BLAS 278 (Ac) and BRM-BLAS 320 (Ac) compounds, thousand of times higher than the protocols described above (800 mcg/Kg, 4.2 mg/Kg and 4.8 mg/Kg, respectively) was perfectly tolerated without evidences of toxicity. The necropsy made after 14 days merely reveals a slight decrease in the white pulp of the spleen, without apparent alterations of the hepatic, renal parenchyma, bone marrow, thymus, suprarenal glands, etc.

We claim:

1. A compound of the formula

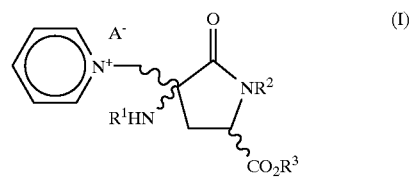

(I)

wherein $R^1$, $R^2$ and $R^3$ are independently selected from H and $COR^4$, $R^4$ being a lower alkyl and aryl; A— is an anion selected from C—, $Ch_3COO$— and OH, and the line means that the corresponding substituent can occupy any of the possibly spatial positions; or a pharmaceutically acceptable salt thereof.

2. A process for preparing a compound of formula (1) as defined in claim 1, comprising reacting L-serine with a molar excess of acetic anhydride and pyridine during a period of time of 15 minutes to 18 hours, at a temperature ranging between 35° C. and the reflux temperature of the reaction mixture in which a crude product is produced corresponding to a mixture of formula (I) compounds, isolating the product through an adsorption chromatography.

3. A compound according to claim 1, wherein $R^4$ is methyl.

4. The compound of claim 1 wherein the compound is 4-ammonium-4-(1-pyridiniomethyl) pyroglutamic acid chloride.

5. The compound of claim 1, wherein the compound is 4-ammonium-4-(1-pyridiniomethyl) pyroglutmatic acid acetate.

6. The compound of claim 1, wherein the compound is 1-acetyl-4-ammonium-4-(1-pyridiniomethyl) pyroglutamic acid dichloride.

TABLE X

LEUKO-LYMOHOCYTE KINETICS AFTER THE IMMUNOMODULATION
GROUP ASSESSEMENT AT DIFFERENT EVOLUTION TIMES
Significance Levels - "p" Values EXPERIMENTAL TIMES (Unique low dose 278 (Ac) vs. UNIQUE HIGH DOSE 320 (Ac))

| EXPERI-MENTAL TIMES | LEUKOCYTES | | | | | | | LYMPHOCYTES | | | | | | |
|---|---|---|---|---|---|---|---|---|---|---|---|---|---|---|
| | FIRST | SECOND | THIRD | FOURTH | FIFTH | SIXTH | SEVENTH | FIRST | SECOND | THIRD | FOURTH | FIFTH | SIXTH | SEVENTH |
| FIRST @ | #### | 0.1357 | 0.1851 | 0.2420 | 0.4502 | 0.2420 | 0.3085 | #### | 0.2743 | 0.1587 | 0.0287 | 0.0228 | 0.0035 | 0.0001 |
| SECOND $ | 0.8357 | #### | 0.4709 | 0.0399 | 0.1158 | 0.0486 | 0.0548 | 0.2743 | #### | 0.4207 | 0.0982 | 0.0050 | 0.0007 | 0.0019 |
| THIRD # | 0.8151 | 0.4300 | #### | 0.0287 | 0.0968 | 0.0399 | 0.0498 | 0.1587 | 0.4207 | #### | 0.0003 | 0.0002 | 0.0001 | 0.0008 |
| FOURTH # | 0.2420 | 0.0350 | 0.0287 | #### | 0.3083 | 0.8868 | 0.4602 | 0.0287 | 0.0012 | 0.0003 | #### | 0.4802 | 0.1240 | 0.2749 |
| FIFTH # | 0.4602 | 0.1858 | 0.0968 | 0.3085 | #### | 0.3085 | 0.3821 | 0.0228 | 0.0030 | 0.0002 | 0.4602 | #### | 0.2189 | 0.3049 |
| SIXTH # | 0.2420 | 0.0045 | 0.0359 | 0.4868 | 0.3085 | #### | 0.4602 | 0.0039 | 0.0007 | 0.0001 | 0.3240 | 0.2809 | #### | 0.3829 |
| SEVENTH # | 0.3084 | 0.0549 | 0.0498 | 0.4620 | 0.3021 | 0.4602 | #### | 0.0068 | 0.0029 | 0.0001 | 0.2743 | 0.3085 | 0.3821 | #### |

Probability levels from the "Statistical tables for Biological, Medical and Agricultural Research, Fisher & Yates, Bdienburgh, Oliver and Lloyd, Liod. 1931"
@; PAUSE
$; LOW DOSE 278 (Ac);
; HIGH DOSE 320 (Ac)

7. The compound of claim 1, wherein the compound is 1-acetyl-4-ammonium-4-(1-pyridiniomethyl) pyroglutamic acid acetate.

8. The compound of claim 1, wherein the compound is 1-acetyl-4-ammonium-4-(1-pyridiniomethyl) pyroglutamic acid chloride.

9. The compound of claim 1, wherein the compound is 1-acetyl-4-ammonium-4-(1-pyridiniomethyl) pyroglutamic acid acetate.

* * * * *